United States Patent
Meehan, Jr.

(10) Patent No.: US 10,064,273 B2
(45) Date of Patent: Aug. 28, 2018

(54) ANTIMICROBIAL COPPER SHEET OVERLAYS AND RELATED METHODS FOR MAKING AND USING

(71) Applicant: MR Label Company, Cincinnati, OH (US)

(72) Inventor: Patrick H. Meehan, Jr., Cincinnati, OH (US)

(73) Assignee: MR Label Company, Cincinnati, OH (US)

( * ) Notice: Subject to any disclaimer, the term of this patent is extended or adjusted under 35 U.S.C. 154(b) by 0 days.

(21) Appl. No.: 14/887,375

(22) Filed: Oct. 20, 2015

(65) Prior Publication Data
US 2017/0111991 A1    Apr. 20, 2017

(51) Int. Cl.
| | | |
|---|---|---|
| H05K 1/09 | (2006.01) | |
| A01N 25/34 | (2006.01) | |
| A01N 59/20 | (2006.01) | |
| H05K 3/22 | (2006.01) | |

(52) U.S. Cl.
CPC .............. *H05K 1/09* (2013.01); *A01N 25/34* (2013.01); *A01N 59/20* (2013.01); *H05K 3/22* (2013.01); *H05K 2201/0929* (2013.01); *H05K 2201/10053* (2013.01)

(58) Field of Classification Search
CPC .... H05K 1/09; H05K 3/22; H05K 2201/0929; H05K 2201/10053; A01N 25/34; A01N 59/20
See application file for complete search history.

(56) References Cited

U.S. PATENT DOCUMENTS

| | | |
|---|---|---|
| 4,906,466 A | 3/1990 | Edwards et al. |
| 5,003,638 A | 4/1991 | Miyake et al. |
| 5,066,328 A | 11/1991 | Zlotnik |
| 5,147,686 A | 9/1992 | Ichimura et al. |
| 5,344,636 A | 9/1994 | Miyata |
| 5,421,867 A | 6/1995 | Yeager et al. |
| 5,494,505 A | 2/1996 | Tomioka et al. |
| 5,571,312 A | 11/1996 | Andoe |
| 5,587,407 A | 12/1996 | Terry et al. |
| 5,753,251 A | 5/1998 | Burrell et al. |
| 5,753,322 A | 5/1998 | Yamaguchi et al. |
| 5,939,087 A | 8/1999 | Hagiwara |
| 6,080,490 A | 6/2000 | Burrell et al. |
| 6,123,925 A | 9/2000 | Barry et al. |
| 6,124,221 A | 9/2000 | Gabbay |
| 6,168,580 B1 | 1/2001 | Yardley |
| 6,180,162 B1 | 1/2001 | Shigeru et al. |

(Continued)

*Primary Examiner* — Hoa C Nguyen
(74) *Attorney, Agent, or Firm* — Calfee, Halter & Griswold LLP

(57) ABSTRACT

Control panels with antimicrobial copper sheet overlays are disclosed. In some embodiments, the antimicrobial copper used in the copper sheet overlays can be selected from copper or copper alloys containing from about 60 to about 100 wt % copper. In other embodiments, the copper sheet overlays have one or more deflection spots to permit an operator to use the control panel to operate an electronic device. Some embodiments include methods to manufacture the control panels comprising antimicrobial copper sheet overlays. Further embodiments include methods for operating an electronic device using the control panels comprising antimicrobial copper sheet overlays.

23 Claims, 10 Drawing Sheets

(56) References Cited

U.S. PATENT DOCUMENTS

| | | |
|---|---|---|
| 6,194,332 B1 | 2/2001 | Rock et al. |
| 6,211,450 B1 | 4/2001 | Ishida |
| 6,213,995 B1 | 4/2001 | Steen et al. |
| 6,228,502 B1 | 5/2001 | Saitoh et al. |
| 6,267,590 B1 | 7/2001 | Barry et al. |
| 6,291,549 B1 | 9/2001 | Mechtel et al. |
| 6,296,863 B1 | 10/2001 | Trogolo et al. |
| 6,303,183 B1 | 10/2001 | Wilczynski et al. |
| 6,313,064 B1 | 11/2001 | Miyafuji et al. |
| 6,322,588 B1 | 11/2001 | Ogle et al. |
| 6,333,093 B1 | 12/2001 | Burrell et al. |
| 6,365,066 B1 | 4/2002 | Podszun et al. |
| 6,365,130 B1 | 4/2002 | Barry et al. |
| 6,365,220 B1 | 4/2002 | Burrell et al. |
| 6,428,858 B1 | 8/2002 | Bolton et al. |
| 6,436,422 B1 | 8/2002 | Trogolo et al. |
| 6,465,042 B2 | 10/2002 | Saitoh et al. |
| 6,482,424 B1 | 11/2002 | Gabbay |
| 6,509,057 B2 | 1/2003 | Shigeru et al. |
| 6,514,622 B1 | 2/2003 | Hayakawa et al. |
| 6,544,440 B1 | 4/2003 | Kozasa et al. |
| 6,548,162 B1 | 4/2003 | Machida et al. |
| 6,565,913 B2 | 5/2003 | Arps et al. |
| 6,575,945 B2 | 6/2003 | Prosl et al. |
| 6,582,715 B1 | 6/2003 | Barry et al. |
| 6,585,767 B1 | 7/2003 | Holley et al. |
| 6,585,813 B2 | 7/2003 | Kiik et al. |
| 6,602,811 B1 | 8/2003 | Rock et al. |
| 6,627,675 B1 | 9/2003 | Finnie et al. |
| 6,649,569 B2 | 11/2003 | Hirsbrunner et al. |
| 6,663,877 B1 | 12/2003 | Du Pont |
| 6,673,433 B1 | 1/2004 | Saeki et al. |
| 6,699,606 B2 | 3/2004 | Machida et al. |
| 6,921,546 B2 | 7/2005 | Albach |
| 6,929,705 B2 | 8/2005 | Myers et al. |
| 6,949,598 B2 | 9/2005 | Terry |
| 7,001,933 B2 | 2/2006 | Lines et al. |
| 7,090,856 B2 | 8/2006 | Qian et al. |
| 7,250,453 B2 | 7/2007 | Sakuma et al. |
| 7,310,824 B2 | 12/2007 | Walsh |
| 7,311,766 B2 | 12/2007 | Nyden et al. |
| 7,311,944 B2 | 12/2007 | Sambasivan et al. |
| 7,335,248 B2 | 2/2008 | Abou-Nemeh |
| 7,357,949 B2 | 4/2008 | Trogolo et al. |
| 7,381,715 B2 | 6/2008 | Sabesan |
| 7,381,751 B2 | 6/2008 | Sarangapan |
| 7,476,698 B2 | 1/2009 | Wagener et al. |
| 7,488,442 B2 | 2/2009 | Matsumoto et al. |
| 7,547,302 B2 | 6/2009 | Porto et al. |
| 7,553,389 B2 | 6/2009 | Sinsel et al. |
| 7,585,902 B2 | 9/2009 | Trogolo |
| 7,595,355 B2 | 9/2009 | Trogolo |
| 7,598,300 B2 | 10/2009 | Trogolo |
| 7,625,576 B2 | 12/2009 | Moskovitz et al. |
| 7,645,824 B2 | 1/2010 | Hendriks |
| 7,659,397 B2 | 2/2010 | Hidaka |
| 7,771,833 B2 | 8/2010 | Ja Chisholm et al. |
| 7,820,284 B2 | 10/2010 | Terry |
| 7,906,132 B2 | 3/2011 | Ziegler et al. |
| 7,910,648 B2 | 3/2011 | Weidman |
| 7,935,428 B2 | 5/2011 | Doye et al. |
| 7,939,149 B2 | 5/2011 | Haskin et al. |
| 7,955,636 B2 | 6/2011 | Terry |
| 7,985,424 B2 | 7/2011 | Tomalia et al. |
| 8,025,120 B2 | 9/2011 | Eddy |
| 8,043,710 B2 | 10/2011 | Jeong et al. |
| 8,066,854 B2 | 11/2011 | Storey et al. |
| 8,092,815 B2 | 1/2012 | Sabesan |
| 8,092,912 B2 | 1/2012 | Veerasamy et al. |
| 8,124,169 B2 | 2/2012 | Ylitalo et al. |
| 8,158,137 B2 | 4/2012 | Bignozzi et al. |
| 8,227,365 B2 | 7/2012 | Nageswaran |
| 8,247,064 B2 | 8/2012 | Zhao et al. |
| 8,282,951 B2 | 10/2012 | Redler |
| 8,361,635 B2 | 1/2013 | Chang et al. |
| 8,377,569 B2 | 2/2013 | Chang et al. |
| 8,383,248 B2 | 2/2013 | Chang et al. |
| 8,383,527 B2 | 2/2013 | Hilfenhaus et al. |
| 8,409,724 B2 | 4/2013 | Chang et al. |
| 8,414,547 B2 | 4/2013 | DiFiore et al. |
| 8,415,023 B2 | 4/2013 | Chang et al. |
| 8,434,487 B2 | 5/2013 | Nelson et al. |
| 8,454,984 B2 | 6/2013 | Krongauz et al. |
| 8,512,417 B2 | 8/2013 | Miller et al. |
| 8,522,585 B1 | 9/2013 | Pratt et al. |
| 8,529,528 B2 | 9/2013 | Robinson et al. |
| 8,530,056 B2 | 9/2013 | Pilloy et al. |
| 8,563,020 B2 | 10/2013 | Uhlmann et al. |
| 8,592,045 B2 | 11/2013 | Olsson |
| 8,603,637 B2 | 12/2013 | Chang et al. |
| 8,609,036 B2 | 12/2013 | Fuller et al. |
| 8,637,590 B2 | 1/2014 | Weidman |
| 8,641,967 B2 | 2/2014 | Bik et al. |
| 8,652,499 B2 | 2/2014 | Nakamura et al. |
| 8,657,943 B2 | 2/2014 | Batista et al. |
| 8,663,796 B2 | 3/2014 | Chang et al. |
| 8,741,437 B2 | 6/2014 | Pilloy et al. |
| 8,753,561 B2 | 6/2014 | Lee et al. |
| 8,765,256 B2 | 7/2014 | Ohrlander et al. |
| 8,778,408 B2 | 7/2014 | Hirota et al. |
| 8,808,724 B2 | 8/2014 | Cichocki et al. |
| 8,821,911 B2 | 9/2014 | Gan et al. |
| 8,828,552 B2 | 9/2014 | Neumann et al. |
| 8,828,710 B2 | 9/2014 | Anderson et al. |
| 8,845,751 B2 | 9/2014 | Link et al. |
| 8,858,775 B2 | 10/2014 | Agg et al. |
| 8,864,149 B2 | 10/2014 | Stryker et al. |
| 8,883,195 B2 | 11/2014 | Bagga et al. |
| 8,889,178 B2 | 11/2014 | Bagga et al. |
| 8,906,515 B2 | 12/2014 | Tomantschger et al. |
| 8,914,924 B2 | 12/2014 | Stryker et al. |
| 8,927,004 B1 | 1/2015 | Dehnad et al. |
| 8,945,363 B2 | 2/2015 | Pickford et al. |
| 9,011,890 B2 | 4/2015 | Wang et al. |
| 9,011,965 B2 | 4/2015 | Gan et al. |
| 9,028,925 B2 | 5/2015 | Shin et al. |
| 9,028,962 B2 | 5/2015 | Borrelli et al. |
| 2001/0026802 A1 | 10/2001 | Price et al. |
| 2001/0040001 A1* | 11/2001 | Toyooka ............... B29C 43/40 156/233 |
| 2002/0033114 A1 | 3/2002 | Suehiro et al. |
| 2002/0110575 A1 | 8/2002 | Gavin et al. |
| 2003/0095230 A1 | 5/2003 | Neely et al. |
| 2003/0118658 A1 | 6/2003 | Trogolo et al. |
| 2003/0152632 A1 | 8/2003 | Sabesan et al. |
| 2003/0194491 A1 | 10/2003 | Gold et al. |
| 2004/0043686 A1 | 3/2004 | Batdorf |
| 2004/0121077 A1 | 6/2004 | Park et al. |
| 2004/0121181 A1 | 6/2004 | Call |
| 2004/0253321 A1 | 12/2004 | Fechner et al. |
| 2004/0253435 A1 | 12/2004 | Nomura |
| 2005/0048218 A1 | 3/2005 | Weidman |
| 2005/0058682 A1 | 3/2005 | Sharratt |
| 2005/0123589 A1 | 6/2005 | Gabbay |
| 2005/0126430 A1 | 6/2005 | Lightner et al. |
| 2005/0129742 A1 | 6/2005 | Bringley et al. |
| 2005/0129929 A1 | 6/2005 | Patton et al. |
| 2005/0129937 A1 | 6/2005 | Patton et al. |
| 2005/0136100 A1 | 6/2005 | Foss |
| 2005/0202099 A1 | 9/2005 | Lo |
| 2006/0124487 A1 | 6/2006 | Brown |
| 2006/0141015 A1 | 6/2006 | Tessier et al. |
| 2006/0166024 A1 | 7/2006 | Ong et al. |
| 2006/0172013 A1 | 8/2006 | Hirai |
| 2006/0182851 A1 | 8/2006 | Kastl |
| 2006/0238857 A1 | 10/2006 | Sander |
| 2006/0251730 A1 | 11/2006 | Lo |
| 2006/0259020 A1 | 11/2006 | Sharratt |
| 2007/0092556 A1 | 4/2007 | Schecter et al. |
| 2007/0110781 A1 | 5/2007 | Kotterer et al. |
| 2007/0134303 A1 | 6/2007 | Yahiaoui et al. |
| 2007/0172661 A1 | 7/2007 | Fechner et al. |
| 2007/0172679 A1 | 7/2007 | Luttgens |
| 2007/0195259 A1 | 8/2007 | Olsson |

(56) References Cited

U.S. PATENT DOCUMENTS

| | | |
|---|---|---|
| 2007/0196605 A1 | 8/2007 | Ong |
| 2007/0231295 A1 | 10/2007 | Hoppe et al. |
| 2007/0243263 A1 | 10/2007 | Trogolo |
| 2007/0254163 A1 | 11/2007 | Veerasamy et al. |
| 2007/0275101 A1 | 11/2007 | Lu et al. |
| 2008/0017307 A1 | 1/2008 | Ong et al. |
| 2008/0026026 A1 | 1/2008 | Lu et al. |
| 2008/0032119 A1 | 2/2008 | Feldhahn et al. |
| 2008/0033522 A1 | 2/2008 | Grewe et al. |
| 2008/0057134 A1 | 3/2008 | Crudden |
| 2008/0060113 A1 | 3/2008 | Walsh |
| 2008/0085326 A1 | 4/2008 | Ruan |
| 2008/0124298 A1 | 5/2008 | Solomon et al. |
| 2008/0147019 A1 | 6/2008 | Song et al. |
| 2008/0161741 A1 | 7/2008 | Bene et al. |
| 2008/0166384 A1 | 7/2008 | Jones |
| 2008/0171068 A1 | 7/2008 | Wyner et al. |
| 2008/0199502 A1 | 8/2008 | Tessier et al. |
| 2008/0213392 A1 | 9/2008 | Nageswaran |
| 2008/0233204 A1 | 9/2008 | Horley et al. |
| 2008/0279809 A1 | 11/2008 | Hackbarth et al. |
| 2009/0025359 A1 | 1/2009 | Chandra et al. |
| 2009/0035341 A1 | 2/2009 | Wagener et al. |
| 2009/0035342 A1 | 2/2009 | Karandikar et al. |
| 2009/0117173 A1 | 5/2009 | Chen et al. |
| 2009/0162695 A1 | 6/2009 | Hevesi et al. |
| 2009/0246292 A1 | 10/2009 | Seville et al. |
| 2009/0280156 A1 | 11/2009 | Hotokebuchi et al. |
| 2009/0324738 A1 | 12/2009 | Krongauz |
| 2010/0015193 A1 | 1/2010 | Inaoka et al. |
| 2010/0021710 A1 | 1/2010 | Hunt et al. |
| 2010/0113871 A1 | 5/2010 | Dias et al. |
| 2010/0136325 A1 | 6/2010 | Reddy et al. |
| 2010/0183894 A1 | 7/2010 | Hyvarinen et al. |
| 2010/0227052 A1 | 9/2010 | Carter et al. |
| 2010/0286790 A1 | 11/2010 | Gruner et al. |
| 2010/0291174 A1 | 11/2010 | Barcikowski et al. |
| 2011/0000616 A1 | 1/2011 | Hanrahan et al. |
| 2011/0038909 A1 | 2/2011 | Roe et al. |
| 2011/0067703 A1 | 3/2011 | Martens et al. |
| 2011/0081530 A1 | 4/2011 | Robinson et al. |
| 2011/0081542 A1 | 4/2011 | Pilloy et al. |
| 2011/0097957 A1 | 4/2011 | Gedanken et al. |
| 2011/0104477 A1 | 5/2011 | Wagener et al. |
| 2011/0123643 A1 | 5/2011 | Biersteker et al. |
| 2011/0155432 A1 | 6/2011 | Tomonari et al. |
| 2011/0195938 A1 | 8/2011 | Wunch et al. |
| 2011/0206817 A1 | 8/2011 | Arnold et al. |
| 2011/0208304 A1 | 8/2011 | Justin et al. |
| 2011/0244256 A1 | 10/2011 | Song et al. |
| 2011/0293742 A1 | 12/2011 | Yang |
| 2011/0311604 A1 | 12/2011 | Xu et al. |
| 2012/0058169 A1 | 3/2012 | Olson et al. |
| 2012/0071807 A1 | 3/2012 | McClure, Jr. |
| 2012/0089068 A1 | 4/2012 | McClure, Jr. |
| 2012/0107592 A1 | 5/2012 | Vasilev et al. |
| 2012/0114878 A1 | 5/2012 | Petrmichl et al. |
| 2012/0135254 A1 | 5/2012 | Kahrom |
| 2012/0141743 A1 | 6/2012 | Kolodziej et al. |
| 2012/0171406 A1 | 7/2012 | Mase et al. |
| 2012/0176858 A1 | 7/2012 | Stenzel et al. |
| 2012/0176860 A1 | 7/2012 | Stenzel et al. |
| 2012/0193232 A1 | 8/2012 | Yu et al. |
| 2012/0225312 A1 | 9/2012 | Chin et al. |
| 2012/0241987 A1 | 9/2012 | Lee |
| 2012/0244381 A1 | 9/2012 | Chang et al. |
| 2012/0244386 A1 | 9/2012 | Chang et al. |
| 2012/0251756 A1 | 10/2012 | Buckley |
| 2012/0261289 A1 | 10/2012 | Wyner et al. |
| 2012/0301528 A1 | 11/2012 | Uhlmann et al. |
| 2012/0301531 A1 | 11/2012 | Uhlmann et al. |
| 2012/0301533 A1 | 11/2012 | Uhlmann et al. |
| 2012/0302703 A1 | 11/2012 | Greiner et al. |
| 2013/0022756 A1 | 1/2013 | Augustine et al. |
| 2013/0022835 A1 | 1/2013 | Chang et al. |
| 2013/0048211 A1 | 2/2013 | Sirlereaux et al. |
| 2013/0053807 A1 | 2/2013 | Taylor et al. |
| 2013/0108702 A1 | 5/2013 | Santra |
| 2013/0110058 A1 | 5/2013 | Adie et al. |
| 2013/0117936 A1 | 5/2013 | Stryker |
| 2013/0171225 A1 | 7/2013 | Uhlmann et al. |
| 2013/0182381 A1 | 7/2013 | Gray et al. |
| 2013/0189323 A1 | 7/2013 | Neumann et al. |
| 2013/0226061 A1 | 8/2013 | Dickson |
| 2013/0230603 A1 | 9/2013 | Liu et al. |
| 2013/0236564 A1 | 9/2013 | Tufts et al. |
| 2013/0244526 A1 | 9/2013 | Wyner et al. |
| 2013/0245568 A1 | 9/2013 | Kerr |
| 2013/0252021 A1 | 9/2013 | Neumann et al. |
| 2013/0272773 A1 | 10/2013 | Kamen et al. |
| 2013/0280471 A1 | 10/2013 | Johansson et al. |
| 2013/0302640 A1 | 11/2013 | Neumann et al. |
| 2013/0315972 A1 | 11/2013 | Krasnow et al. |
| 2014/0005616 A1 | 1/2014 | Moreland et al. |
| 2014/0041403 A1 | 2/2014 | Anderson et al. |
| 2014/0077488 A1 | 3/2014 | Wegener et al. |
| 2014/0084019 A1 | 3/2014 | Cotey |
| 2014/0099357 A1 | 4/2014 | Vachon et al. |
| 2014/0141263 A1 | 5/2014 | Jones et al. |
| 2014/0154292 A1 | 6/2014 | Borrelli et al. |
| 2014/0158510 A1 | 6/2014 | Cliff et al. |
| 2014/0170238 A1 | 6/2014 | Cliff et al. |
| 2014/0220331 A1 | 8/2014 | Lord et al. |
| 2014/0224519 A1* | 8/2014 | Mallak .................. H01H 23/04 174/66 |
| 2014/0227334 A1 | 8/2014 | Mallak et al. |
| 2014/0230510 A1 | 8/2014 | Pratt et al. |
| 2014/0236112 A1 | 8/2014 | Von Wolff et al. |
| 2014/0271757 A1 | 9/2014 | Agrawal et al. |
| 2014/0287012 A1 | 9/2014 | Lee et al. |
| 2014/0308867 A1 | 10/2014 | Van Emmerick et al. |
| 2014/0319000 A1 | 10/2014 | Fishberger et al. |
| 2014/0328721 A1 | 11/2014 | Pratt et al. |
| 2014/0329110 A1 | 11/2014 | Pratt et al. |
| 2014/0329111 A1 | 11/2014 | Pratt et al. |
| 2014/0345087 A1 | 11/2014 | Simon et al. |
| 2014/0356605 A1 | 12/2014 | Adib et al. |
| 2014/0376596 A1* | 12/2014 | Karabinis ............. G01K 1/083 374/208 |
| 2014/0377318 A1 | 12/2014 | Cornell |
| 2015/0004361 A1 | 1/2015 | Culpepper |
| 2015/0010605 A1 | 1/2015 | Charme Delgado |
| 2015/0010715 A1 | 1/2015 | Cook et al. |
| 2015/0076187 A1 | 3/2015 | Cohen |
| 2015/0086597 A1* | 3/2015 | Mallak .................. A01N 59/16 424/407 |
| 2015/0099095 A1 | 4/2015 | Pershin et al. |
| 2015/0111673 A1 | 4/2015 | Tomantschger et al. |
| 2015/0147372 A1 | 5/2015 | Agrawal et al. |
| 2015/0238056 A1* | 8/2015 | Fellhoelter ......... A47K 10/3687 242/560 |

* cited by examiner

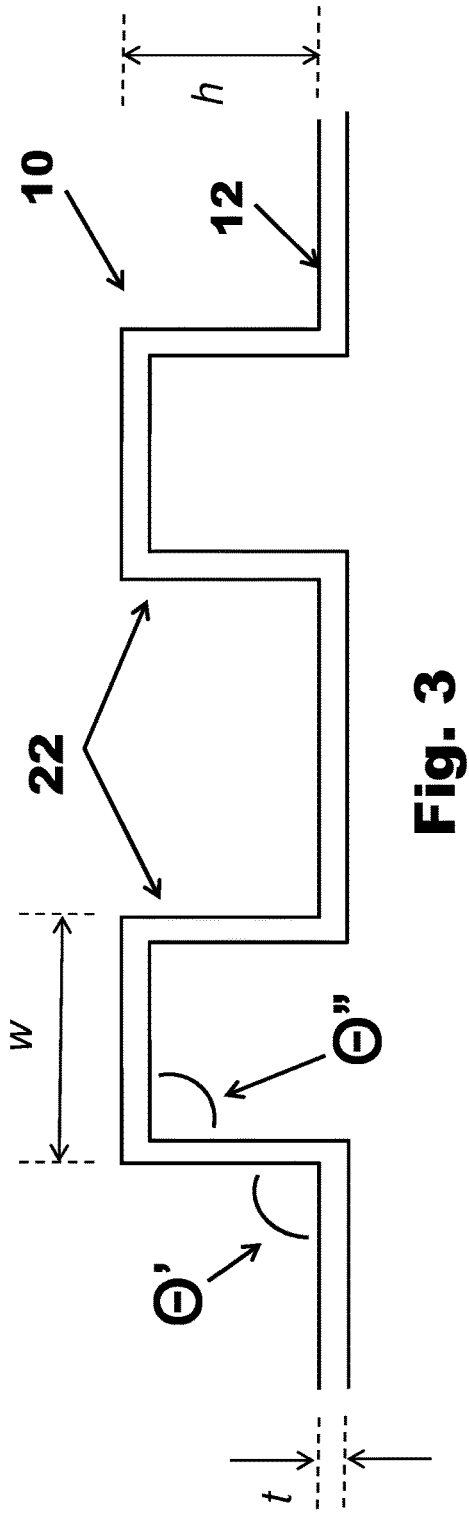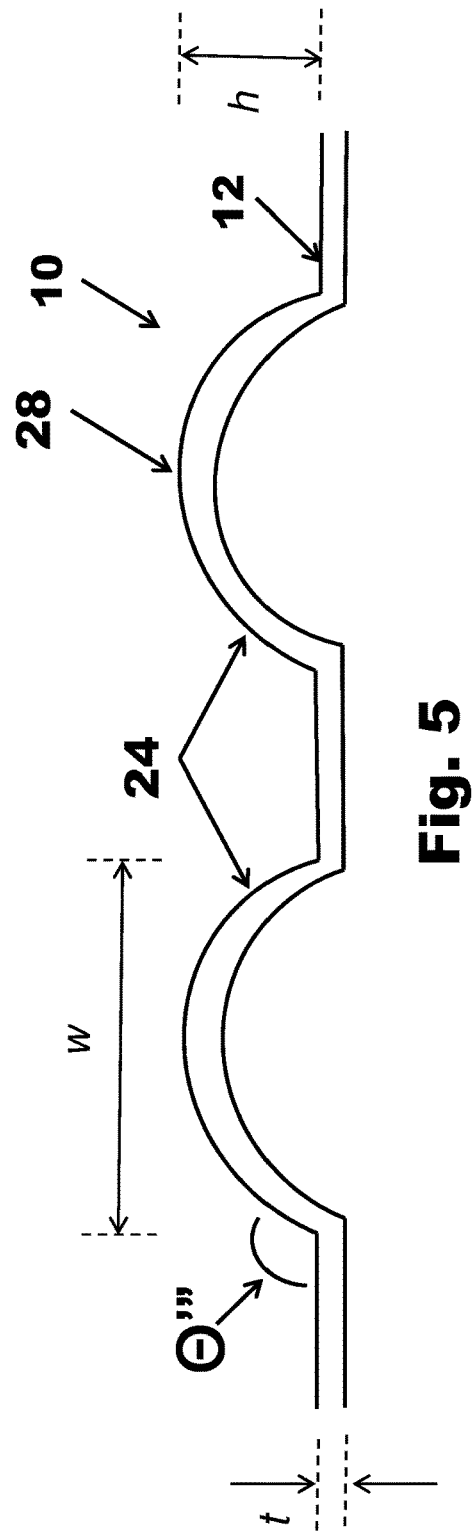

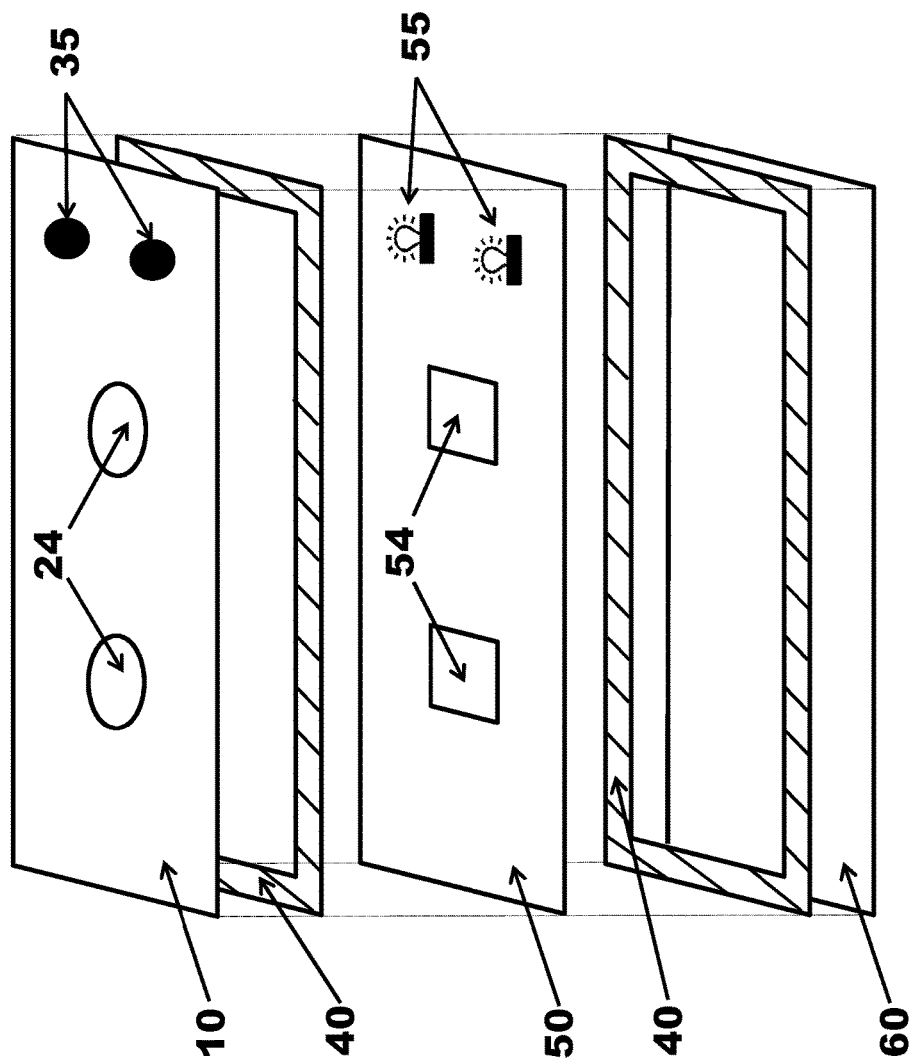

ANTIMICROBIAL COPPER SHEET OVERLAYS AND RELATED METHODS FOR MAKING AND USING

BACKGROUND

Microbes, such as bacteria, can be transmitted by hand-to-hand or hand-to surface contact. In certain instances, the transmission of microbes (e.g., antibiotic-resistant microbes) can be a serious health problem and can sometimes lead to infections that can spread quickly or that may be difficult to treat. Sometimes this transmission can occur in locations housing people with weakened immune systems, such as but not limited to hospitals, nursing homes, or elder care facilities. An in-hospital infection by an antibiotic-resistant microbe can increase the cost of a patient's treatment by tens of thousands of dollars.

Some embodiments of the present invention address one or more of the above-discussed deficiencies or problems.

SUMMARY

In some embodiments, the present disclosure is directed to a control panel surface that comprises an antimicrobial copper sheet overlay, which can, in some instances, have at least one deflection spot. The antimicrobial copper sheet overlay can have, for example, a thickness t from about 0.002 inches to about 0.008 inches. In certain embodiments, the antimicrobial copper sheet overlay can comprise copper or a copper alloy comprising from about 60 wt % to about 100 wt % copper. In yet other embodiments, the copper or copper alloy can be tempered to be ¼ hard, ½ hard, ¾ hard, hard, extra hard, or spring. The copper or copper alloy can sometimes have a tensile strength of from about 350 N/mm$^2$ to about 600 N/mm$^2$. In some embodiments, the control panel surface can comprise an antimicrobial copper sheet overlay with more than one deflection spots. In other embodiments, the antimicrobial copper sheet overlay can be printed on an area other than the deflection spot. In still other embodiments, the antimicrobial copper sheet overlay can further comprise one or more perforations. In some examples, the antimicrobial copper sheet overlay can be part of a control panel.

In some embodiments, the present disclosure is directed to a control panel comprising a control panel surface and a circuit board where the control panel surface can comprise an antimicrobial copper sheet overlay with at least one deflection spot and where the deflection spot can, in some instances, be located over a switch (e.g., a membrane switch or a hardwire switch) on the circuit board. In other embodiments, the control panel surface can comprise more than one antimicrobial copper sheet overlays, each with at least one deflection spot, and the deflection spot on each antimicrobial copper sheet overlay can be located over a switch on the circuit board. In some embodiments, the control panel can comprise more than one circuit board, and in further embodiments, each deflection spot on the antimicrobial copper sheet overlay can be located over a switch on at least one circuit board. In some instances, the antimicrobial copper sheet overlay has a thickness t from about 0.002 inches to about 0.008 inches. In other instances, the antimicrobial copper sheet overlay can comprise copper or a copper alloy comprising from about 60 wt % to about 100 wt % copper. In still other embodiments, the copper or copper alloy can be tempered to be ¼ hard, ½ hard, ¾ hard, hard, extra hard, or spring. The antimicrobial copper sheet overlay can, in some embodiments, comprise copper or a copper alloy comprising from about 60 wt % to about 100 wt % copper. The copper or copper alloy can, in certain embodiments, have a tensile strength of from about 350 N/mm$^2$ to about 600 N/mm$^2$. In some embodiments, the control panel surface can comprise an antimicrobial copper sheet overlay with more than one deflection spot. The control panel surface can, in some instances, comprise an antimicrobial copper sheet overlay with at least one deflection spot that is embossed. The antimicrobial copper sheet overlay can, in some examples, be printed on an area other than the deflection spot. The antimicrobial copper sheet overlay can comprise one or more perforations, in certain examples. In some embodiments, one or more (e.g., all) of the at least one deflection spots on the antimicrobial copper sheet overlay can withstand a finger press at a force of about 4.5 N for at least about 100,000 cycles without the antimicrobial copper sheet overlay being damaged.

In some embodiments, the present disclosure is directed to a method of making a control panel surface by providing an antimicrobial copper sheet and printing at least one graphic on the surface of the antimicrobial copper sheet to indicate the location of a deflection spot. In other embodiments, the method of making a control panel surface can comprise embossing the antimicrobial copper sheet to indicate the location of the deflection spot. In some embodiments, the antimicrobial copper sheet overlay can have a thickness t from about 0.002 inches to about 0.008 inches. In yet other embodiments, the antimicrobial copper sheet overlay can comprise copper or a copper alloy comprising from about 60 wt % to about 100 wt % copper. In some examples, the copper or copper alloy can be tempered to be ¼ hard, ½ hard, ¾ hard, hard, extra hard, or spring. In still other embodiments, the graphic can be printed on a location of the surface of the antimicrobial sheet other than the location of the deflection spot. In some embodiments, the method of making a control panel surface can comprise printing more than one graphics on the surface of the antimicrobial copper sheet to indicate the location of more than one deflection spots. In some examples, the antimicrobial copper sheet overlay can comprise one or more perforations.

In some embodiments, the present disclosure is directed to a method of making a control panel. For example, the control panel can be made by (a) providing an antimicrobial copper sheet, (b) printing at least one graphic on the surface of the antimicrobial copper sheet to indicate the location of at least one deflection spot, (c) forming an antimicrobial copper sheet overlay from the antimicrobial copper sheet printed with at least one graphic, (d) providing a circuit board comprising at least one switch, and (e) placing the antimicrobial copper sheet overlay over the circuit board, such that the deflection spot on the antimicrobial copper sheet is located over the switch on the circuit board. In certain instances, the antimicrobial copper sheet can be embossed (e.g., at the location of the deflection spot) to indicate the location of the deflection spot. In some examples, the antimicrobial copper sheet overlay can have a thickness t from about 0.002 inches to about 0.008 inches. In other examples, the antimicrobial copper sheet overlay can comprise copper or a copper alloy comprising from about 60 wt % to about 100 wt % copper. In some embodiments, the antimicrobial copper sheet can be printed with more than one graphics on the surface of the antimicrobial copper sheet to indicate the location of more than one deflection spots. The antimicrobial copper sheet overlay can comprise, in some instances, one or more perforations.

In some embodiments, the present disclosure is directed to a method of operating an electronic device, by providing an electronic device and a control panel where the control panel has a control panel surface comprising an antimicrobial copper sheet overlay comprising at least one deflection spot, and a circuit board under the control panel surface comprising a switch located under the deflection spot; one or more of deflection spots on the antimicrobial copper sheet overlay can be pressed to operate the electronic device. In some embodiments, the antimicrobial copper sheet can be printed with at least one graphic. In other embodiments, one or more deflection spots on the antimicrobial copper sheet overlay can be embossed. In still other embodiments, the antimicrobial copper sheet overlay can have a thickness t from about 0.002 inches to about 0.008 inches. In further embodiments, the antimicrobial copper sheet overlay can comprise copper or a copper alloy can comprise from about 60 wt % to about 100 wt % copper. In still additional embodiments, the control panel has a control panel surface that can comprise an antimicrobial copper sheet overlay comprising more than one deflection spot, and a circuit board under the control panel surface that can comprise a switch located under each deflection spot. In some examples, the antimicrobial copper sheet overlay also can comprise one or more perforations.

BRIEF DESCRIPTION OF THE DRAWINGS

FIG. 3 is a cross-sectional view of the copper sheet overlay of FIG. 2 along line A-A';

FIG. 5 is a cross-sectional view of the copper sheet overlay of FIG. 4 along line B-B';

FIG. 11 is an exploded view of an exemplary embodiment of a control panel of the present disclosure comprising one copper sheet overlay and one circuit board.

DETAILED DESCRIPTION

Figure 1:
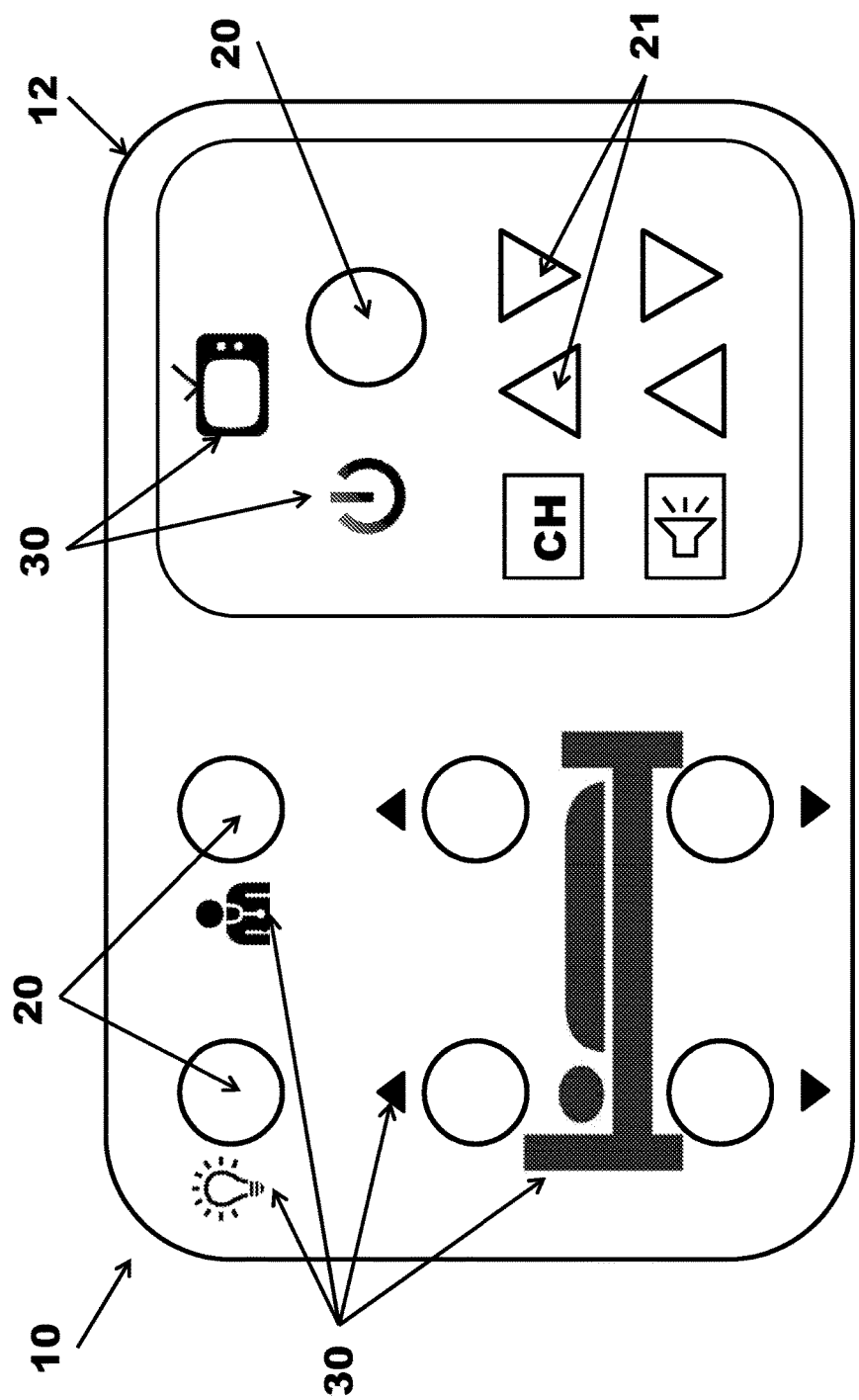
FIG. 1 is a top view of an exemplary embodiment of a copper sheet overlay of a control panel of the present disclosure.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments, of the present invention relate to a control panel for an electronic device, wherein the surface of the control panel comprises a copper sheet overlay, which may be made from antimicrobial copper, to reduce or eliminate microbial contamination.

Other embodiments of the present disclosure are directed to a control panel comprising a copper sheet overlay. The copper sheet overlay of the control panel can comprise one or more deflections spots for operating the control panel, and thereby operating the controlled electronic device. In some embodiments, the copper sheet overlay of the control panel comprises more than one embossed deflection spots for operating the control panel. In some embodiments, the one or more deflection spots on the control panel may overlay corresponding membrane switches on a circuit board located beneath the copper sheet overlay of the control panel. In some embodiments, the one or more deflection spots on the control panel may overlay corresponding hardwire switches on a circuit board located beneath the copper sheet overlay of the control panel.

Other embodiments of the present disclosure are directed to a method of making a control panel surface by providing an antimicrobial copper sheet and printing one or more graphics on the surface of the antimicrobial copper sheet to indicate the location of one or more deflection spots. In some embodiments, the deflection spots may be embossed. In some embodiments, the one or more deflection spots on the control panel may overlay corresponding membrane switches on a circuit board located beneath the copper sheet overlay of the control panel. In some embodiments, the one or more deflection spots on the control panel may overlay corresponding hardwire switches on a circuit board located beneath the copper sheet overlay of the control panel.

Yet other embodiments of the present disclosure are directed to a method of making a control panel. The control panel is made by providing an antimicrobial copper sheet and a circuit board comprising at least one switch. The antimicrobial copper sheet is printed with one or more graphics on the surface of the antimicrobial copper sheet to indicate the location of one or more deflection spots, and an antimicrobial copper sheet overlay is formed from the printed antimicrobial copper sheet. The antimicrobial copper sheet overlay is placed over the circuit board such that each deflection spot on the antimicrobial copper sheet are located over a switch on the circuit board.

In some embodiments, the present disclosure is directed to a method of operating an electronic device, by providing an electronic device and a control panel. The control panel has a control panel surface comprising an antimicrobial copper sheet overlay comprising one or more deflection spots, and a circuit board under the control panel surface comprising a switch located under each deflection spot. The deflection spot on the antimicrobial copper sheet overlay is pressed to operate the electronic device.

For the purpose of the present disclosure, the following terms are defined:

The terms "copper" and "copper alloy" as used herein, unless otherwise specified, refer to metallic copper and metallic alloys of copper with other elements. Unless otherwise specified, the term "copper" should be understood to include both pure metallic copper and metallic copper alloys.

The term "copper sheet" as used herein, unless otherwise specified, refers to metallic copper or metallic copper alloys formed into thin, flat pieces that are significantly larger in length (i.e., x-direction) and width (i.e., y-direction) than in thickness (i.e., z-direction). Copper sheets typically have a thickness no greater than about 0.1 inches (about 2.5 mm).

The term "antimicrobial copper" as used herein refers to metallic copper or metallic copper alloys that are registered with the U.S. Environmental Protection Agency (EPA) as approved to provide supplemental antimicrobial action between routine cleanings of environmental or touch surfaces in home, public, and healthcare settings.

The term "control panel" as used herein, unless otherwise specified, refers to an electronic device used to activate, change the settings of, and otherwise operate an electronic device. In some embodiments, a control panel comprises a control panel surface and an underlying circuit board.

The term "control panel surface" refers to the exterior, outward-facing portion of a control panel. A control panel surface is touched by and interfaces with the operator. Typically, a control panel will comprise one or more control devices, including but not limited to deflection spots, buttons, toggles, knobs, slide bars, or combinations of such devices, that are manipulated by the operator. Manipulation of the control devices by the operator causes the underlying circuit board of the control panel to generate and send electronic signals to the electronic device.

The term "copper sheet overlay" as used herein, unless otherwise specified, refers to a control panel surface made of a sheet of antimicrobial metallic copper. The copper sheet overlay may be of any suitable shape, including but not limited to a square, a circle, a rectangle, an oval, a star (e.g., 3, 4, 5, 6, 7, 8, or 9 pointed), a triangle, a hexagon, or other acceptable shape. The corners of the copper sheet overlay, if present, may in some embodiments be rounded (e.g., partially rounded). The copper sheet overlay as a whole may be substantially flat (i.e., planar), or the copper sheet overlay may be curved or bent (e.g., along one or more axes) to create a three dimensional shape. In certain embodiments, one or more edges of the copper sheet overlay can be bent (e.g., at about 0 degrees, about 10 degrees, about 45 degrees, about 90 degrees, about 135 degrees, about 170 degrees, or about 180 degrees) to create one or more lips along one or more edges.

The term "deflection spot" refers a region of the copper sheet overlay that is intended to be touched or pressed to operate a switch on the underlying circuit board of the control panel. A deflection spot is positioned to overlay a switch on the underlying circuit board. A deflection spot may be of appropriate size for activation by a human finger or hand, i.e., encompassing an area of from about 0.0625 $in^2$ to about 9 $in^2$ (about 0.4 $cm^2$ to about 60 $cm^2$). A deflection spot may be in the general shape of a square, a circle, a rectangle, an oval, a triangle, a hexagon, or other acceptable shape. A deflection spot may be flush with, or raised or recessed relative to, the surface level of the control panel surface surrounding the deflection spot. The locations of deflections spots on a control panel surface may be identified by the operator through visual markings or tactile indicators.

The term "electronic device" as used herein, unless otherwise specified, refers generally to any electronic equipment that is activated, operated, or controlled via a control panel. In some embodiments, an electronic device may be operated via a control panel that is frequently touched by more than one person. Examples of electronic devices include, but are not limited to, hospital beds, television sets, room lighting systems, intercom systems, laboratory testing equipment, automatic teller machines, exercise equipment, and so forth.

The term "emboss" as used herein, unless otherwise specified, refers to an area of a sheet-like material that is raised (or depressed) relative to the surrounding surface level of the object. The term "embossing" as used herein, unless otherwise specified, refers to a process of creating the raised (or depressed) areas of a sheet-like material.

The term "graphics" as used herein, unless otherwise specified, refers to pictures, icons, letters, or words that are printed onto the surface of an object. The term "symbols" as used herein, unless otherwise specified, refers to pictures, icons, letters, or words that are embossed onto the surface of an object.

The term "useful life" as used herein, unless otherwise specified, refers to an interval of time in which the copper sheet overlay experiences normal handling or operation at least once daily, for at least about 50% of the days during the interval of time, without the copper sheet overlay experiencing sufficient damage (e.g., breaking, cracking, denting, thinning) to render the control panel inoperable.

The copper used in the copper sheet overlays for control panels of the present disclosure in some embodiments may comprise copper or copper alloys suitable for antimicrobial use. Specifically, the copper sheet may comprise a copper or copper alloy selected from the list of antimicrobial copper materials that are registered with the U.S. Environmental Protection Agency (EPA) as approved to provide supplemental antimicrobial action between routine cleanings of environmental or touch surfaces in home, public, and healthcare settings. In some embodiments, antimicrobial copper may comprise from about 60 wt % to about 100 wt % copper, with any remaining components comprising metals or other elements suitable for use in the control panel surfaces of the present disclosure. In some embodiments, antimicrobial copper may comprise from about 65 wt % to about 98 wt % copper, including from about 70 wt % to about 95 wt % copper, including from about 75 wt % to about 92 wt % copper, including from about 76 wt % to about 91 wt % copper, including from about 78 wt % to about 90 wt % copper, including from about 80 wt % to about 89 wt % copper, including from about 82 wt % to about 88 wt % copper, and including from about 85 wt % to about 87 wt % copper. Some suitable antimicrobial copper alloy elements include, but are not limited to, nickel, iron, tin, zinc, aluminum, manganese, and combinations thereof. Some embodiments of the antimicrobial copper materials include alloys that are a mixture of copper, nickel, iron, zinc, and manganese. In some embodiments, the antimicrobial copper alloy comprises about 87 wt % copper, 10 wt % nickel, 1 wt % iron, 1 wt % manganese, and 1 wt % zinc by weight of the alloy. In some embodiments, the antimicrobial copper alloy comprises about 76 wt % copper, 21 wt % nickel, 1 wt % iron, 1 wt % manganese, and 1 wt % zinc by weight of the alloy.

In some embodiments, one or both surfaces of the copper used for the copper sheet overlay may be smooth (i.e., no texture or microtexture visible to the naked eye). In some embodiments, one or both surfaces of the copper used for the copper sheet overlay may be textured or microtextured. In some embodiments, one or both surfaces of the copper sheet overlay may be textured or microtextured by any suitable technique, including but not limited to sanding, sand blasting, engraving, etching, brushing, and so forth. In some embodiments, a texture or microtexture on one or both copper surfaces may help adhesive bond to the copper sheet overlay The copper sheets of the present disclosure may be of a suitable thickness for use as control panel surfaces. In some embodiments, the copper sheet will be thick enough to be sufficiently rugged for the present purpose. In other embodiments, the copper sheet is thick enough to prevent tearing during fabrication, or being scratched, broken, torn, or otherwise damaged during operation of the control panel. In some embodiments, the copper sheet is thin enough to allow the deflection spots of the control panel to be easily depressed with a level of force that is comfortable for an operator's finger, particularly if the operator is a child or an adult that is weakened by disease or age. In some embodiments, suitable thicknesses t of copper sheeting may range from about 0.0015" to about 0.012" (about 0.04 mm to about 0.3 mm), including from about 0.002" to about 0.01" (about 0.05 mm to about 0.25 mm), from about 0.0025" to about 0.009" (about 0.065 mm to about 0.23 mm), from about 0.003" to about 0.008" (about 0.08 mm to about 0.2 mm), including from about 0.0035" to about 0.0075" (about 0.09 mm to about 0.19 mm), from about 0.004" to about 0.007" (about 0.1 mm to about 0.18 mm), from about 0.0045" to about 0.0065" (about 0.11 mm to about 0.17 mm), from about 0.005" to about 0.006" (about 0.13 mm to about 0.15 mm), and including from about 0.0055" to about 0.006" (about 0.14 mm to about 0.15 mm).

In certain embodiments, the copper sheet overlay has a useful life of at least about 1 year. In certain embodiments, the copper sheet overlay has a useful life of from about 1 year to about 30 years. In certain embodiments, the copper sheet overlay has a useful life of from about 2 years to about 25 years, including from about 3 years to about 20 years, including from about 4 years to about 15 years, including from about 5 years to about 12 years, including from about 6 years to about 10 years, and including from about 7 years to about 8 years. In certain embodiments, the copper sheet overlay has a useful life of at least about 2 years, at least about 3 years, at least about 5 years, at least about 7 years, at least about 10 years, at least about 12 years, and at least about 15 years.

The copper sheets of the present disclosure may be of any suitable temper for use as control panel surfaces. "Temper" refers to the condition produced in a metal by mechanical or thermal treatment. The temper of a metal corresponds to characteristic structural and mechanical properties, such as tensile strength and hardness. Typical mechanical properties for various tempers of two exemplary copper alloys are shown in Table 1.

enough to resist being scratched, cut, or similarly damaged during use and cleaning. In other embodiments, the copper sheet is tempered to be soft enough to allow the deflection spots of the control panel to be easily depressed with a level of force that is comfortable for an operator's finger, particularly if the operator is a child or an adult that is weakened by disease or age. In some embodiments, copper sheets suitable for the present invention may be tempered to ¼ hard, ½ hard, ¾ hard, hard, extra hard, or spring temper.

The copper sheet overlay of the control panel of the present disclosure comprises one or more deflection spots, which is a region of the copper sheet overlay that is intended to be touched or pressed to operate a switch on the underlying circuit board of the control panel. In some embodiments, a deflection spot may be flush with the surface level of the copper sheet overlay surrounding the deflection spot. In some embodiments, a deflection spot may be embossed to be raised or recessed relative to the surface level of the copper sheet overlay surrounding the deflection spot. The locations of deflections spots on the copper sheet overlay may be identified by the operator through visual markings or tactile indicators.

A deflection spot may be any suitable shape, including but not limited to a square, a circle, a rectangle, an oval, a star (e.g., 3, 4, 5, 6, 7, 8, or 9 pointed), a triangle, a hexagon, or other acceptable shape. In some embodiments, a deflection spot may be of appropriate size for activation by a human finger or hand, i.e., encompassing an area of from about 0.0625 in$^2$ to about 9 in$^2$ (about 0.4 cm$^2$ to about 60 cm$^2$), including from about 0.09 in$^2$ to about 6 in$^2$ (about 0.6 cm$^2$ to about 40 cm$^2$), including from about 0.15 in$^2$ to about 4 in$^2$ (about 1 cm$^2$ to about 25 cm$^2$), including from about 0.25 in$^2$ to about 2.5 in$^2$ (about 1.6 cm$^2$ to about 16 cm$^2$), including from about 0.5 in$^2$ to about 2 in$^2$ (about 3 cm$^2$ to about 13 cm$^2$), and including from about 0.75 in$^2$ to about 1 in$^2$ (about 5 cm$^2$ to about 6 cm$^2$).

In some embodiments, a deflection spot may have a width w of about 0.25" to about 3" (about 0.6 cm to about 7.5 cm), including from about 0.3" to about 2.5" (about 0.75 cm to about 6.25 cm), including from about 0.4" to about 2" (about 1 cm to about 5 cm), including from about 0.5" to about 1.6" (about 1.25 cm to about 4 cm), including from about 0.7" to about 1.4" (about 1.75 cm to about 3.5 cm), including from

TABLE 1

| | Alloy A[1] | | | Alloy B[2] | | |
|---|---|---|---|---|---|---|
| Temper | Tensile Strength (N/mm$^2$) | Yield Strength (N/mm$^2$) | % Elongation | Tensile Strength (N/mm$^2$) | Yield Strength (N/mm$^2$) | % Elongation |
| Soft/Annealed | 295-345 | 130 | 35 | 295-365 | 145 | 40 |
| ¼Hard | 350-460 | 365 | 12 | 325-435 | 275 | 15 |
| ½Hard | 400-495 | 435 | 5 | 385-485 | 395 | 5 |
| Hard | 490-570 | 515 | >1 | 460-545 | 485 | 2 |
| Extra Hard | 505-585 | 525 | >1 | 495-580 | 515 | >1 |
| Spring | 540-604 | >525 | <1 | 540-600 | 545 | <2 |

[1]Alloy A comprises about 87% copper, 10% nickel, 1% iron, 1% manganese, and 1% zinc by weight.
[2]Alloy B comprises about 76% copper, 21% nickel, 1% iron, 1% manganese, and 1% zinc by weight.

In some embodiments, the copper sheet is tempered to be hard enough to be sufficiently rugged for the present purpose. In other embodiments, the copper sheet is tempered to be hard enough to prevent bending, denting, or deforming when the deflection spots are pressed. Similarly, in some embodiments, the copper sheet is tempered to be hard about 0.8" to about 1" (about 2 cm to about 2.5 cm), and including from about 0.9" to about 1" (about 2.25 cm to about 2.5 cm).

In some embodiments, a deflection spot may have a height h of from about 0 mm to about 5 mm, including from about 0.1 mm to about 5 mm, including from about 0.2 mm to about 4 mm, including from about 0.3 mm to about 3 mm, including from about 0.4 mm to about 2.5 mm, including from about 0.5 mm to about 2 mm, including from about 0.6 mm to about 1.5 mm, and including from about 0.7 mm to about 1 mm.

In some embodiments, a deflection spot may have a vertical travel length (i.e., the distance the deflection spot moves when pressed) of from about 0.1 mm to about 5 mm, including from about 0.2 mm to about 4 mm, including from about 0.3 mm to about 3 mm, including from about 0.4 mm to about 2.5 mm, including from about 0.5 mm to about 2 mm, including from about 0.6 mm to about 1.5 mm, and including from about 0.7 mm to about 1 mm. In some embodiments, the vertical travel length of the embossed area may be approximately equal to the height h of the embossed area. In some embodiments, the vertical travel length of the embossed area may be less than the height h of the embossed area. In some embodiments, the vertical travel length of the embossed area may be greater than the height h of the embossed area.

In some embodiments, the deflection spot should be able to withstand a finger press at a force of about 1 pound-force (4.5 N) for at least about 100,000 cycles without the deflection spot being stretched, deformed, dented, cracked, or otherwise damaged. In some embodiments, the deflection spot should be able to withstand a finger press at a force of about 1 pound-force (4.5 N) for at least about 150,000 cycles, including at least about 200,000 cycles, including at least about 250,000 cycles, and including at least about 300,000 cycles, without the deflection spot being stretched, deformed, dented, cracked, or otherwise damaged. In some embodiments, the deflection spot should be able to withstand a finger press at a force of about 2 pound-force (9 N) for at least about 150,000 cycles, including at least about 200,000 cycles, including at least about 250,000 cycles, and including at least about 300,000 cycles, without the deflection spot being stretched, deformed, dented, cracked, or otherwise damaged.

In some embodiments, the copper sheet overlay of the control panel of the present disclosure is of unitary design. In some instances, there are no gaps or crevices around the deflection spots to catch and hold dirt, and the unitary design of the copper sheet overlay makes the control panel surface easy to clean. In certain embodiments, the unitary design of the copper sheet overlay makes it easy to overlay the copper sheet overlay onto the circuit board of the control panel, and to seal the copper sheet overlay, circuit board, and other components of the control panel within a sturdy exterior housing. In other embodiments, the unitary design of the copper sheet overlay thereby protects the electronic components within the control panel from contamination by dirt or liquids during use and routine cleaning.

In some embodiments, the control panel of the present disclosure may comprise more than one copper sheet overlay, where each copper sheet overlay is of unitary design. In some instances, there are no gaps or crevices around the deflection spots to catch and hold dirt, and the unitary design of each copper sheet overlay makes the control panel surface easy to clean. In some embodiments, the unitary design of each copper sheet overlay makes it easy to place each copper sheet overlay over the appropriate region of the circuit board of the control panel, and to seal the copper sheet overlays, circuit board, and other components of the control panel within a sturdy exterior housing. In some embodiments, the unitary design of each copper sheet overlay makes it easy to place each copper sheet overlay over the appropriate regions of more than one circuit boards of the control panel, and to seal the copper sheet overlays, circuit boards, and other components of the control panel within a sturdy exterior housing. In certain embodiments, the unitary design of each copper sheet overlay thereby protects the electronic components within the control panel from contamination by dirt or liquids during use and routine cleaning.

The copper sheet overlay of the control panel of the present disclosure may be manufactured from roll stock of antimicrobial copper sheeting. The copper sheet overlay may be fabricated using any suitable sheet metal converting methods, such as but not limited to die cutting, punching, stamping, pressing, embossing, and so forth. The copper sheet overlay may be formed to be any suitable shape, including but not limited to a square, a circle, a rectangle, an oval, a star (e.g., 3, 4, 5, 6, 7, 8, or 9 pointed), a triangle, a hexagon, or other acceptable shape. The corners of the copper sheet overlay, if present, may in some embodiments be rounded (e.g., partially rounded). In some embodiments, the copper sheet overlay as a whole may be substantially flat (i.e., planar), excepting any embossed areas at the deflection spots. In some embodiments, the copper sheet overlay may be curved or bent to create a three dimensional shape for the control panel surface.

In some embodiments, the copper sheet overlay may be embossed with deflection spots and/or symbols, using any suitable embossing technique. In some embodiments, the copper sheet overlay may also be printed with graphics, using any suitable printing technique. In certain embodiments, the adhesive may be applied to the outward- or inward-facing sides of the copper sheet overlay, to adhere the copper sheet overlay to the circuit board, spacing components, sealing gaskets, or exterior housing (e.g., back and edge pieces) of the control panel.

The copper sheet overlay of the control panel of the present disclosure may be embossed or otherwise molded to form embossed areas that are raised (or depressed) areas at the deflection spots on the control panel surface. In certain instances, the embossed areas provide visual and tactile indications of the deflection spot on the control panel surface. In some embodiments, the embossed areas may also give the operator tactile feedback that the deflection spot has been adequately pressed when the operator is using the control panel.

In some embodiments, an embossed area may be of appropriate size for activation by a human finger or hand, i.e., encompassing an area of from about 0.06 in$^2$ to about 9 in$^2$ (about 0.4 cm$^2$ to about 60 cm$^2$), including from about 0.09 in$^2$ to about 6 in$^2$ (about 0.6 cm$^2$ to about 40 cm$^2$), including from about 0.15 in$^2$ to about 4 in$^2$ (about 1 cm$^2$ to about 25 cm$^2$), including from about 0.25 in$^2$ to about 2.5 in$^2$ (about 1.6 cm$^2$ to about 16 cm$^2$), including from about 0.5 in$^2$ to about 2 in$^2$ (about 3 cm$^2$ to about 13 cm$^2$), and including from about 0.75 in$^2$ to about 1 in$^2$ (about 5 cm$^2$ to about 6 cm$^2$).

In some embodiments, a deflection spot may have a width w of about 0.25" to about 3" (about 0.6 cm to about 7.5 cm), including from about 0.3" to about 2.5" (about 0.75 cm to about 6.25 cm), including from about 0.4" to about 2" (about 1 cm to about 5 cm), including from about 0.5" to about 1.6" (about 1.25 cm to about 4 cm), including from about 0.7" to about 1.4" (about 1.75 cm to about 3.5 cm), including from about 0.8" to about 1" (about 2 cm to about 2.5 cm), and including from about 0.9" to about 1" (about 2.25 cm to about 2.5 cm).

In some embodiments, a deflection spot may have a height h of from about 0 mm to about 5 mm, including from about 0.1 mm to about 5 mm, including from about 0.2 mm to about 4 mm, including from about 0.3 mm to about 3 mm, including from about 0.4 mm to about 2.5 mm, including from about 0.5 mm to about 2 mm, including from about 0.6 mm to about 1.5 mm, and including from about 0.7 mm to about 1 mm.

In some embodiments, an embossed area may have a vertical travel length (i.e., the distance the embossed area deflects when pressed) of from about 0.1 mm to about 5 mm, including from about 0.2 mm to about 4 mm, including from about 0.3 mm to about 3 mm, including from about 0.4 mm to about 2.5 mm, including from about 0.5 mm to about 2 mm, including from about 0.6 mm to about 1.5 mm, and including from about 0.7 mm to about 1 mm. In some embodiments, the vertical travel length of the embossed area may be approximately equal to the height h of the embossed area. In some embodiments, the vertical travel length of the embossed area may be less than the height h of the embossed area. In some embodiments, the vertical travel length of the embossed area may be greater than the height h of the embossed area.

The embossed area may be any suitable shape, including but not limited to a square, a circle, a rectangle, an oval, a star (e.g., 3, 4, 5, 6, 7, 8, or 9 pointed), a triangle, a hexagon, or other acceptable shape. The corners of the embossed area, if present, may in some embodiments, be rounded (e.g., partially rounded) to form a more pleasing tactile surface for the operator's fingers. In some embodiments, the embossed area should be able to withstand a finger press at a force of about 1 pound-force (4.5 N) for at least about 100,000 cycles without the embossed area of the copper sheet overlay being stretched, deformed, dented, cracked, or otherwise damaged. In some embodiments, the embossed area should be able to withstand a finger press at a force of about 1 pound-force (4.5 N) for at least about 150,000 cycles, including at least about 200,000 cycles, including at least about 250,000 cycles, and including at least about 300,000 cycles, without the embossed area of the copper sheet overlay being stretched, deformed, dented, cracked, or otherwise damaged. In some embodiments, the embossed area should be able to withstand a finger press at a force of about 2 pound-force (9 N) for at least about 150,000 cycles, including at least about 200,000 cycles, including at least about 250,000 cycles, and including at least about 300,000 cycles, without the embossed area being stretched, deformed, dented, cracked, or otherwise damaged.

In some embodiments, illustrated in FIG. 1, the copper sheet overlay 10 comprises a copper sheet 12. The copper sheet 12 may be flat, with printed graphics surrounding deflection spots 20, 21 that are flush with the surface of the copper sheet overlay. In FIG. 1, the copper sheet overlay 10 represents the control panel surface of a controller for a hospital bed. The deflection spots 20, 21 overlay switches on the control panel circuit board. Pressing the deflection spots 20, 21 causes elastic deformation of the copper sheet overlay, which allows the underside of the copper sheet overlay to contact and depress the switch under the deflection spots. Pressing the deflection spots 20, 21 thereby allows the operator to control an electronic device via electronic signals generated by the switches on the circuit board. The printed graphics surrounding the deflection spots may be in the form of circles, triangles, or other acceptable shapes. Additional graphics 30 may be printed on the copper sheet overlay to indicate the function (e.g., head or foot elevation of the bed, television channel or volume, light switch, and nurse intercom) of the deflection spots.

Figure 2:
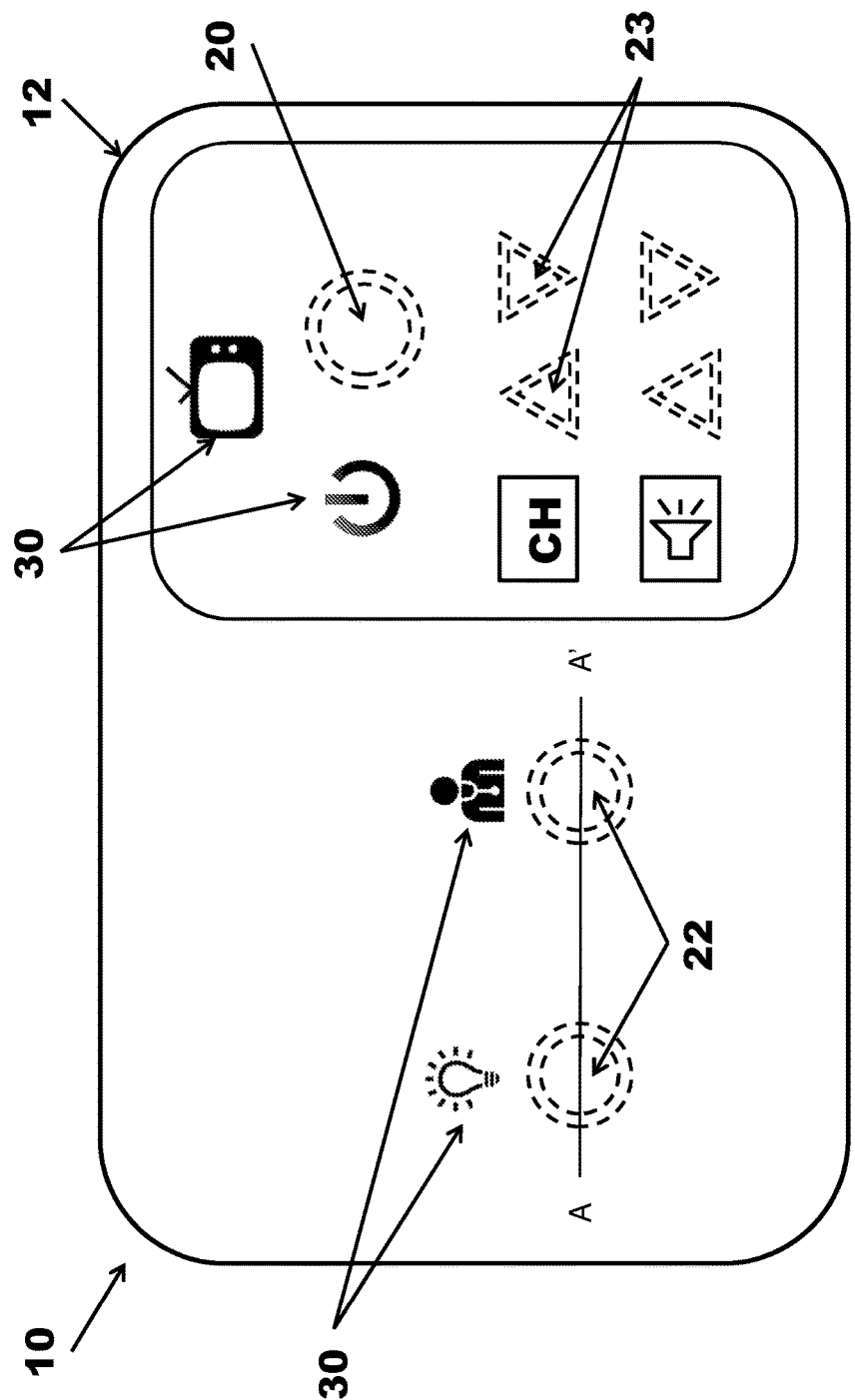
FIG. 2 is a top view of another exemplary embodiment of a copper sheet overlay of a control panel of the present disclosure.
Figure 4:
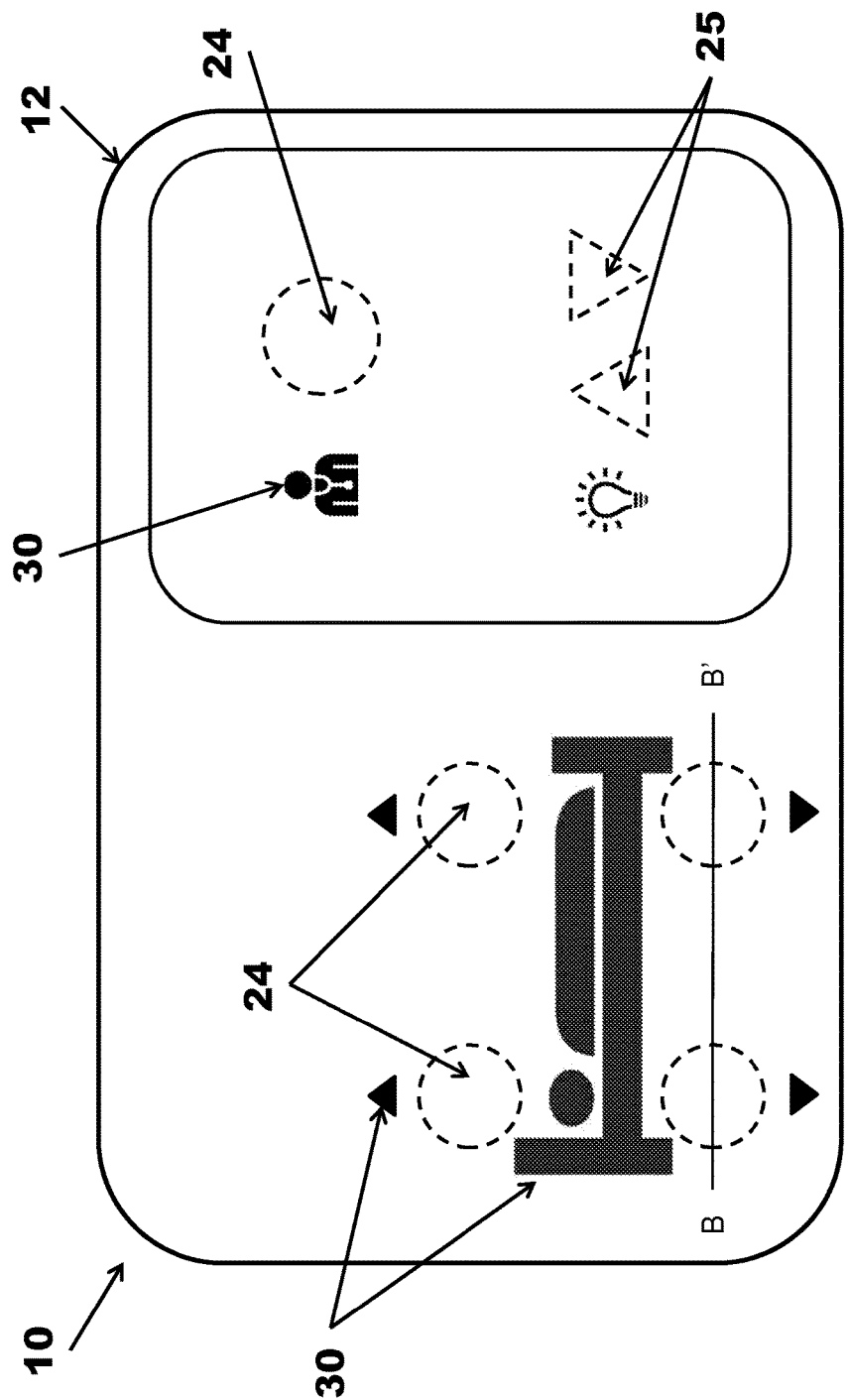
FIG. 4 is a top view of another exemplary embodiment of a copper sheet overlay of a control panel of the present disclosure.
Figure 6:
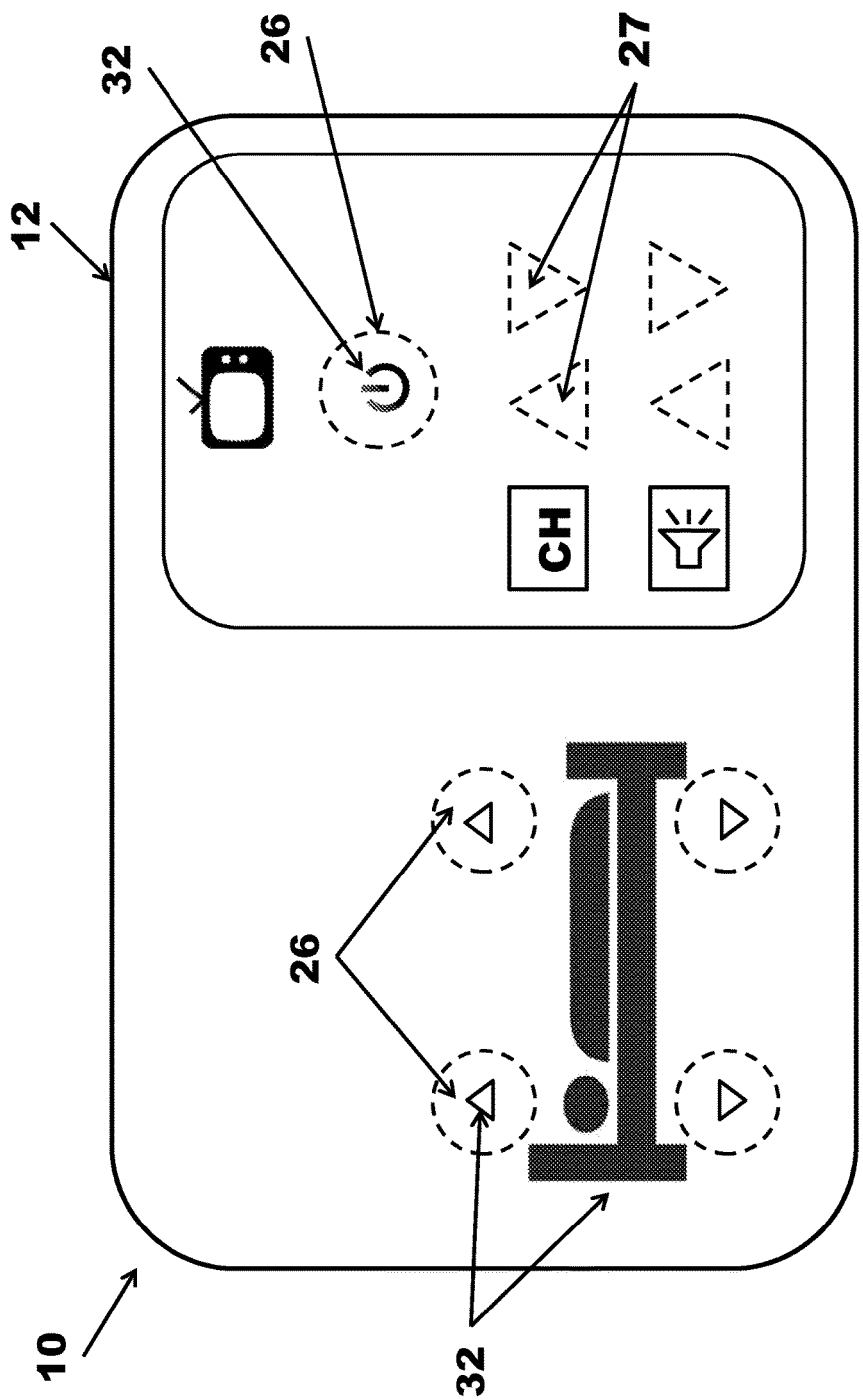
FIG. 6 is a top view of another exemplary embodiment of a copper sheet overlay of a control panel of the present disclosure.

In some embodiments, such as those illustrated in FIG. 2, the copper sheet overlay 10 comprises a copper sheet 12. The copper sheet 12 may be embossed with one or more traditional raised embossed areas. In FIG. 2, the copper sheet overlay 10 represents the control panel surface of a controller for a hospital bed. The deflection spots 22, 23 are embossed in a traditional raised emboss profile, forming raised regions on the control panel surface that overlay switches on the control panel circuit board. (For the purpose of this disclosure, the dashed lines in FIGS. 2, 4, and 6 represent bending lines where the copper sheet overlay is bent to form embossed areas.) Pressing the deflection spots 22, 23 causes elastic deformation of the copper sheet overlay, which allows the underside of the copper sheet overlay to contact and depress the switch under the deflection spots. Pressing the deflection spots 22, 23 thereby allows the operator to control an electronic device via electronic signals generated by the switches on the circuit board. The deflection spots may be embossed in any suitable form, such as circles 22, triangles 23, or other acceptable shapes. Graphics 30 may be printed on the copper sheet overlay to indicate the function (e.g., head or foot elevation of the bed, television channel or volume, light switch, and nurse intercom) of the deflection spots.

FIG. 3 illustrates a cross-sectional view of the copper sheet overlay 10, viewed along the line A-A' of FIG. 2. The copper sheet overlay is made from a sheet of copper 12 that has a thickness t, which may range from about 0.0015" to about 0.012" (about 0.04 mm to about 0.3 mm). The copper sheet overlay has been embossed with a traditional raised emboss profile, with an emboss height it, of from about 0.1 mm to about 5 mm, and an emboss width w, of from about 0.6 cm to about 7.5 cm. The traditional raised emboss profile is characterized by bending lines with bending angles $\Theta'$ at the base and bending angles $\Theta''$ at the top of the embossed profile. In some embodiments, the bending angles $\Theta'$ and $\Theta''$ can be the same or different and can be from about 45° to about 135°, from about 60° to about 120°, from about 80° to about 105°, from about 85° to 95°. In some embodiments, the bending angles $\Theta'$ and $\Theta''$ can be the same and are about 90°.

In some embodiments, such as those illustrated in FIG. 4, the copper sheet overlay 10 comprises a copper sheet 12. The copper sheet 12 may be embossed with one or more pillow embossed areas. In this example, the copper sheet overlay 10 represents the control panel surface of a controller for a hospital bed. The deflection spots 24, 25 are embossed in a embossed profile, forming raised regions on the control panel surface that overlay switches on the control panel circuit board. Pressing the deflection spots 24, 25 causes elastic deformation of the copper sheet overlay, which allows the underside of the copper sheet overlay to contact and depress the switch under the deflection spots. Pressing the deflection spots 24, 25 thereby allows the operator to control an electronic device via electronic signals generated by the switches on the circuit board. The deflection spots may be embossed in any suitable form, such as circles 24, triangles 25, or other acceptable shapes. Graphics 30 may be printed on the copper sheet overlay to indicate the function (e.g., head or foot elevation of the bed, television channel or volume, light switch, and nurse intercom) of the deflection spots. In some embodiments, the copper sheet overlay may be embossed with one or more traditional raised embossed areas, one or more pillow embossed areas, or combinations thereof.

FIG. 5 illustrates a cross-sectional view of the copper sheet overlay 10, viewed along the line B-B' of FIG. 4. The copper sheet overlay is made from a sheet of copper 12 that has a thickness t, which may range from about 0.0015" to about 0.012" (about 0.04 mm to about 0.3 mm). The copper sheet overlay has been embossed with a pillow emboss profile, with an emboss height h of from about 0.1 mm to about 5 mm and an emboss width w of from about 0.6 cm to about 7.5 cm. The pillow emboss profile is characterized by bending lines with bending angles $\Theta'''$ at the base of the embossed profile. In some embodiments of the pillow emboss profile, these bending angles $\Theta'''$ are from about 90° to about 150°, from about 105° to about 145°, or from about 120° to 140°. In other embodiments, $\Theta'''$ is an oblique angle. In certain embodiments, the central area 28 of the pillow-embossed deflection spot comprises a rounded, dome-like profile rather than the flatter top of the traditional raised emboss profile. In some instances, the pillow emboss profile may be more tactilely pleasing to the operator (e.g., compared to the traditional emboss profile) because the pillow emboss has no sharp corners or edges.

In some embodiments, the deflection spots are the regions of the copper sheet overlay that will be most frequently touched by operators. For the copper sheet overlay to retain its antimicrobial properties and provide supplemental antimicrobial action between routine cleanings of the control panel surface, in some embodiments these deflection spots are not overprinted, lacquered, or otherwise coated with another substance that will cover the antimicrobial copper surface. However, in some instances, suitable graphics may be printed on the copper sheet overlay of the control panel near the deflection spots to indicate the functions controlled by the deflection spots located on the copper sheet overlay. Examples of suitable graphics 30 are shown in FIGS. 1, 2, and 4 to indicate the function (e.g., head or foot elevation of the bed, television channel or volume, light switch, and nurse intercom) of the deflection spots on the copper sheet overlay 10.

The copper sheet overlay of the control panel may be printed by any suitable technique including but not limited to flexographic, rotogravure, lithographic, or screen printing. In some embodiments, the copper sheet overlay of the control panel may be printed by a screen printing process. In other embodiments, the ink system for printing on the copper sheet overlay adheres to the copper sheet overlay without rubbing off, chipping, smearing, or fading. In some embodiments, a single color of ink (e.g., black, blue, green, red, etc.) is used to print graphics on the copper sheet overlay. In some embodiments, multiple colors of ink (e.g., black, blue, green, red, etc.) are used to print graphics on the copper sheet overlay. In some embodiments, the color of the ink used to print graphics on the copper sheet overlay may be intended to indicate the function of the deflection spot (e.g., a yellow graphic indicates lighting control, a red graphic indicates a call button, etc.). Any suitable ink system can be used with the copper sheet overlay. Examples of ink systems that are suitable for use with the copper sheet overlay include but are not limited to the 4000 series (with catalyst), the 9600 series (with catalyst), the 1600 series (with catalyst), the 1800 series (with catalyst), and the 3400 series (with catalyst), provided by Nazdar Ink Technologies (Shawnee, Kans., US).

In certain embodiments, the copper sheet overlay of the control panel of the present disclosure may be embossed with suitable symbols, such as, directly on the deflection spots or near the deflection spots, to indicate the functions controlled by the deflection spots. In some embodiments, such as those illustrated in FIG. 6, the copper sheet overlay 10 comprises a copper sheet 12 that may be embossed with one or more embossed areas to form the deflection spots 26 and 27, and symbols 32 are also embossed directly onto some of the embossed deflection spots. (For the purpose of this disclosure, the symbols 32 in FIG. 6 are embossed, not printed.) The embossed symbols may, in some instances, be raised (i.e., elevated) or lowered (i.e., depressed) relative to the top surface level of the deflection spot on the copper sheet overlay of the control panel.

In some embodiments, the copper sheet overlay of the control panel may be both printed with graphics and embossed with symbols to indicate the functions controlled by the deflection spots.

Some examples of the manufacture of the copper sheet overlay include embossing the copper sheet to create raised (or depressed) areas at the deflection spots on the control panel surface. The copper sheets may be embossed by any suitable method. In some embodiments, the copper sheet overlays are embossed using a clamshell embosser. A clamshell embosser has two mated (i.e., male and female) plates that are tooled with the embossing pattern. With the clamshell embosser open, the copper sheet overlay to be embossed is placed between the mated plates. The clamshell embosser is closed and pressurized, which presses the embossing pattern into the copper sheet overlay. The clamshell embosser is then opened, and the copper sheet overlay is removed.

In some embodiments, the copper sheet overlay may be cut to a final shape to fit the end product (i.e., control panel). In some instances, the copper sheet overlay may be perforated by any suitable metalworking method (e.g., punching, drilling, boring, etc.). In some instances, the copper sheet overlay may be finished by any suitable metalworking method, e.g., deburring to remove sharp edges and burrs.

Some embodiments of the manufacture of the copper sheet overlay comprise applying adhesive and, optionally, release liners at predefined locations on the outward- and/or inward-facing sides of the copper sheet overlay, so that, in certain instances, the copper sheet overlay may be adhered to other components of the control panel when the control panel is being assembled. Any suitable adhesive can be applied. In some embodiments, the adhesive system is chosen for the copper sheet overlay to be compatible with all substrates used in the control panel assembly. In other embodiments, the adhesive system is chosen for the copper sheet overlay to durably bond the components to withstand both long-term use and frequent cleaning. Examples of suitable adhesive systems include but are not limited to 3M300LSE, 3M467, and 3M468, all provided by The 3M Company (St. Paul, Minn., US), and V-344 and V-606, both provided by FLEXcon (Spencer, Mass., US). In some embodiments, the surface of the copper sheet overlay may be smooth (i.e., no applied texture or microtexture) where the adhesive is applied. In some embodiments, the surface of the copper sheet overlay may be textured or microtextured where the adhesive is applied. In some embodiments, the surface of the copper sheet overlay may be textured or microtextured (or both) using any suitable technique, including but not limited to sanding, sand blasting, engraving, etching, brushing, and so forth. In some embodiments, a texture on the copper sheet overlay may help the adhesive bond to the copper. In some embodiments, a release liner is applied to the surface of the adhesive facing away from the copper sheet overlay. Any suitable release liner can be applied. Examples of suitable release liners include paper, polymer coated paper, and polymer film release liners coated with silicone or non-silicone release coatings. Suitable release liners may be provided by The 3M Company (St. Paul, Minn., US), Rayven, Inc. (St. Paul, Minn., US) or Drytac Corporation, (Richmond, Va., US).

Some embodiments of the invention include assembling the control panel. In some embodiments, the control panel is assembled from the copper sheet overlay, circuit board, spacing components, sealing gaskets, and housing components, by any suitable method.

Figure 7:
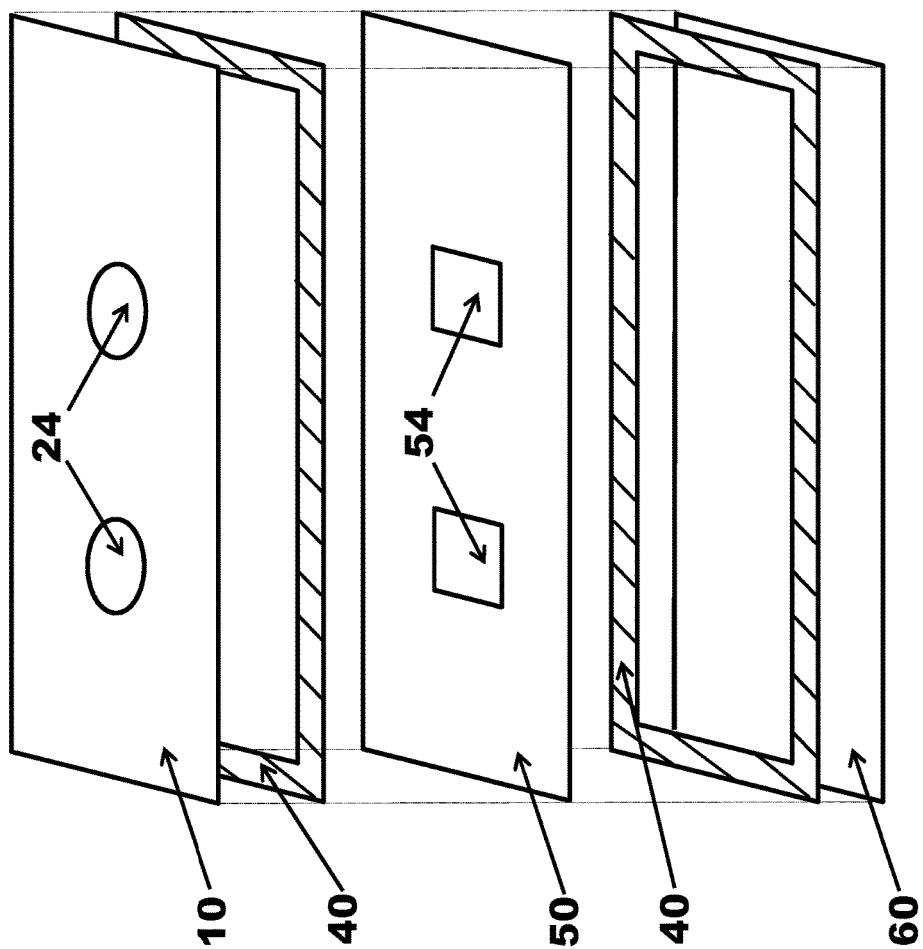
FIG. 7 is an exploded view of an exemplary embodiment of a control panel of the present disclosure comprising one copper sheet overlay and one circuit board.

FIG. 7 is an exploded view of some embodiments of a control panel of the present disclosure comprising a copper sheet overlay and a circuit board. In FIG. 7, the copper sheet overlay 10 may be assembled with a circuit board 50 and a back housing component 60. Spacing components 40 (e.g., gaskets, washers, films, etc.) may optionally be placed between the copper sheet overlay 10 and the circuit board 50, and also optionally between the circuit board 50 and the back housing component 60, to prevent the copper sheet overlay or back housing component from accidentally impacting the circuit board. Deflection spots 24 on the copper sheet overlay 10 are positioned to overlay switches 54 on the circuit board 50 when the control panel is fully assembled. The switches 54 may be any suitable switch mechanism, including but not limited to membrane switches and hardwire switches. During assembly, side and front housing components (not shown) may be attached to hold the copper sheet overlay 10, the circuit board 50, the back housing component 60, and the optional spacing components 40 in place. Sealing gaskets (not shown) may be attached where the housing components join the other components, to provide liquid-tight seals where the control panel components are joined, thereby preventing liquids, dust, and contaminants from entering the interior portion of the control panel.

Figure 8:
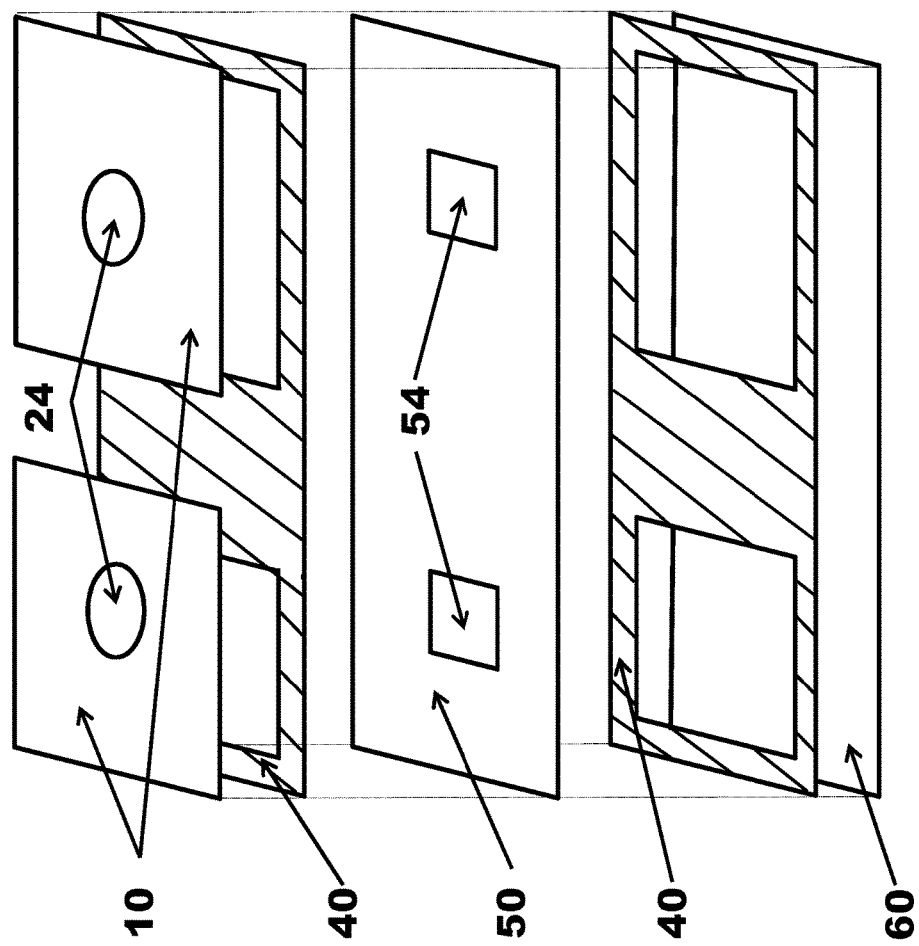
FIG. 8 is an exploded view of an exemplary embodiment of a control panel of the present disclosure comprising two copper sheet overlays and one circuit board.

FIG. 8 is an exploded view of some embodiments of a control panel of the present disclosure comprising a plurality of copper sheet overlays and one circuit board. In FIG. 8, two copper sheet overlays 10 may be assembled with a circuit board 50 and a back housing component 60. Spacing components 40 may optionally be placed between the copper sheet overlays 10 and the circuit board 50, and also optionally between the circuit board 50 and the back housing component 60, to prevent the copper sheet overlays or back housing component from accidentally impacting the circuit board. Deflection spots 24 on the copper sheet overlays 10 are positioned to overlay switches 54 on the circuit board 50 when the control panel is fully assembled. The switches 54 may be any suitable switch mechanism, including but not limited to membrane switches and hardwire switches. During assembly, side and front housing components (not shown) may be attached to hold the copper sheet overlays 10, the circuit board 50, the back housing component 60, and the optional spacing components 40 in place. Sealing gaskets (not shown) may be attached where the housing components join the other components, to provide liquid-tight seals where the control panel components are joined, thereby preventing liquids, dust, and contaminants from entering the interior portion of the control panel.

Figure 9:
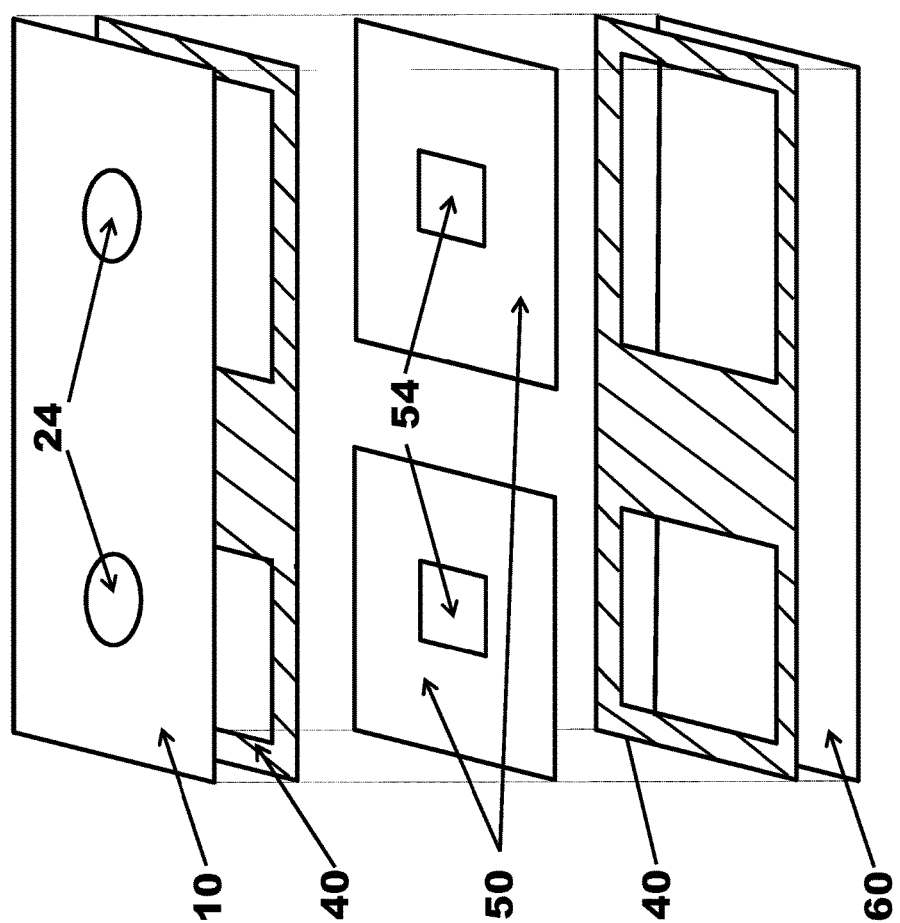
FIG. 9 is an exploded view of an exemplary embodiment of a control panel of the present disclosure comprising one copper sheet overlay and two circuit boards.

FIG. 9 is an exploded view of some embodiments of a control panel of the present disclosure comprising a copper sheet overlay and a plurality of circuit boards. In FIG. 9, one copper sheet overlay 10 may be assembled with two circuit boards 50 and a back housing component 60. Spacing components 40 may optionally be placed between the copper sheet overlay 10 and the circuit boards 50, and also optionally between the circuit boards 50 and the back housing component 60, to prevent the copper sheet overlay or back housing component from accidentally impacting the circuit boards. Deflection spots 24 on the copper sheet overlay 10 are positioned to overlay switches 54 on the circuit boards 50 when the control panel is fully assembled. The switches 54 may be any suitable switch mechanism, including but not limited to membrane switches and hardwire switches. During assembly, side and front housing components (not shown) may be attached to hold the copper sheet overlay 10, the circuit boards 50, the back housing component 60, and the optional spacing components 40 in place. Sealing gaskets (not shown) may be attached where the housing components join the other components, to provide liquid-tight seals where the control panel components are joined, thereby preventing liquids, dust, and contaminants from entering the interior portion of the control panel.

Figure 10:
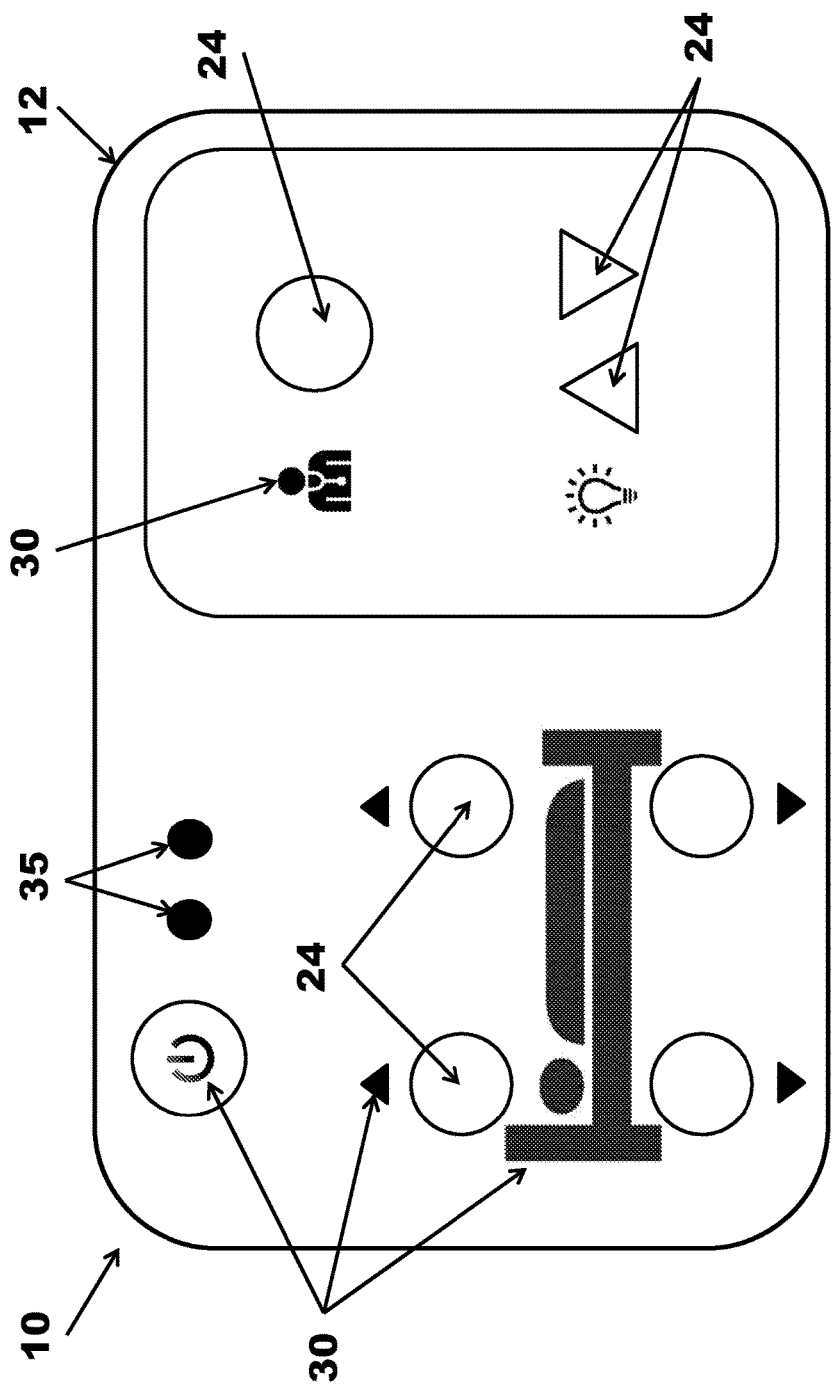
FIG. 10 is a top view of another exemplary embodiment of a copper sheet overlay of a control panel of the present disclosure.

In some embodiments, the copper sheet overlay may be perforated during manufacture to provide one or more perforations through which the user may view lighting elements on the underlying circuit board. The one or more perforations may be of any suitable shape, including but not limited to a square, a circle, a rectangle, an oval, a star (e.g., 3, 4, 5, 6, 7, 8, or 9 pointed), a triangle, a hexagon, or other acceptable shape. Each of the one or more perforations can have any suitable area, such as but not limited to an area of from about 0.06 in$^2$ to about 9 in$^2$ (about 0.4 cm$^2$ to about 60 cm$^2$), including from about 0.09 in$^2$ to about 6 in$^2$ (about 0.6 cm$^2$ to about 40 cm$^2$), including from about 0.15 in$^2$ to about 4 in$^2$ (about 1 cm$^2$ to about 25 cm$^2$), including from about 0.25 in$^2$ to about 2.5 in$^2$ (about 1.6 cm$^2$ to about 16 cm$^2$), including from about 0.5 in$^2$ to about 2 in$^2$ (about 3 cm$^2$ to about 13 cm$^2$), and including from about 0.75 in$^2$ to about 1 in$^2$ (about 5 cm$^2$ to about 6 cm$^2$). The copper sheet overlay can sometimes have 1, 2, 3, 4, 5, 6, 7, 8, 9, 10, 11, 12, 13, 14, 15, 16, 17, 18, 19, 20, or at least 20 perforations. In some instances, the copper sheet overlay can have one or more than one perforation. One or more perforations can be at any suitable place on the copper sheet overlay including but not limited to at or near a deflection spot, at or near an embossed deflection spot, at or near a graphic, or at or near another perforation. As illustrated in FIG. 10, the copper sheet overlay 10 can comprise a copper sheet 12. The copper sheet 12 may have printed graphics surrounding deflection spots 24 that are flush with the surface of the copper sheet overlay, or the copper sheet 12 may be embossed to indicate the position of each deflection spot 24. Additional graphics 30 may be printed on the copper sheet overlay to indicate the function (e.g., head or foot elevation of the bed, television channel or volume, light switch, and nurse intercom) of each deflection spot. The copper sheet 12 may comprise one or more perforations 35 which pass through the copper sheet 12. The one or more perforations 35 allow a user of the control panel to view lighting elements (e.g., light emitting diodes, incandescent light bulbs, fluorescent light bulbs, phosphorescent spots, etc.) positioned on a circuit board below the copper sheet overlay 10. In some embodiments, the perforations 35 may be covered by transparent or translucent covering materials (e.g., glass plate, glass cap, polymer film, polymer plug, etc.) that seal the perforated areas against impinging liquids, dust, or other contaminants, while allowing a user to view the lighting element beneath the copper sheet overlay. In some embodiments, the transparent or translucent covering material may be positioned on the outer surface or the inner surface of the copper sheet overlay to cover the perforations 35. In some embodiments, the transparent or translucent covering material may be inserted into the perforations 35 (e.g., the covering material is in the form of a plug).

FIG. 11 is an exploded view of some embodiments of a control panel of the present disclosure comprising a copper sheet overlay and a circuit board. In FIG. 11, the copper sheet overlay 10 may be assembled with a circuit board 50 and a back housing component 60. Spacing components 40 (e.g., gaskets, washers, films, etc.) may optionally be placed between the copper sheet overlay 10 and the circuit board 50, and also optionally between the circuit board 50 and the back housing component 60, to prevent the copper sheet overlay or back housing component from accidentally impacting the circuit board. Deflection spots 24 on the copper sheet overlay 10 are positioned to overlay switches 54 on the circuit board 50 when the control panel is fully assembled. The switches 54 may be any suitable switch mechanism, including but not limited to membrane switches and hardwire switches. Perforations 35 through the copper sheet overlay 10 are positioned to overlay lighting elements 55 on the circuit board 50 when the control panel is fully assembled. The lighting elements 55 may be any suitable lighting element, including but not limited to light-emitting diodes, incandescent bulbs, and fluorescent bulbs. The lighting elements 55 may emit light of any suitable color that can be visually detected by most human users. In some embodiments, the lighting elements 55 may be color-coded to visually indicate information to a user (e.g., a red light indicates "power off" and a green light indicates "power on"). During assembly, side and front housing components (not shown) may be attached to hold the copper sheet overlay 10, the circuit board 50, the back housing component 60, and the optional spacing components 40 in place. Sealing gaskets (not shown) may be attached where the housing components join the other components, to provide liquid-tight seals where the control panel components are joined, thereby preventing liquids, dust, and contaminants from entering the interior portion of the control panel.

In certain embodiments, during assembly of the control panel, adhesive may be applied to the outward- or inward-facing sides of the copper sheet overlay, to bond the copper sheet overlay to other components of the control panel. In other embodiments, during the manufacture of the copper sheet overlay, adhesive and, optionally, release liners may be applied to the copper sheet overlay at predefined locations as described above. In certain instances, during assembly of the control panel, the optional release liners may be removed from the copper sheet overlay to expose the adhesive applied to the copper sheet overlay, allowing the copper sheet overlay to be bonded to other components of the control panel.

Some embodiments of the invention include using the control panel. For example, a control panel comprising a copper sheet overlay may be used for any suitable purpose including but not limited to activating, operating, or controlling an electronic device. In some embodiments, the control panel may be an integral part of the electronic device being controlled, the control panel may be attached to the electronic device via one or more electronic cables, the control panel may operate wirelessly to control the electronic device, or combinations thereof. In some embodiments, the control panel operates two or more functions of the electronic device (e.g., the control panel operates both speed and slope of a treadmill). In some embodiments, the control panel operates two or more electronic devices (e.g., a call button and a television). In some embodiments, the control panel does not operate a single electronic device (e.g., only room lighting or only a television). In some embodiments, the copper sheet overlay for the control panel surface is manipulated by the operator to operate the electronic device. In some embodiments, the deflection spots on the copper sheet overlay for the control panel is pressed by the operator to operate the electronic device. Examples of uses for control panels of the present disclosure include, but are not limited to, operating hospital beds, television sets, room lighting, fuel (e.g., gasoline or diesel) pumps, intercom systems, laboratory testing equipment, automatic teller machines, exercise equipment, and so forth.

In some embodiments, the copper sheet overlay of the control panel of the present disclosure is sufficiently rugged to withstand repeated cleaning of the control panel surface. In certain embodiments, the copper sheet overlay can provide supplemental antimicrobial action between cleanings (e.g., routine cleanings). In other embodiments, the copper sheet overlay of the control panel can withstand repeated, vigorous cleaning using the strong cleaning solutions (e.g., bleach solutions) and scrubbing protocols employed in medical, clinical, hospital, nursing, or elder care facilities. In yet other embodiments, the copper sheet overlay of the control panel is frequently cleaned (e.g., hourly, every two hours, every six hours, every 12 hours, or daily).

In some embodiments, the copper sheet overlay for the control panel of the present disclosure may be of unitary design. In some instances, there is no gap or crevice around the deflection spots (e.g., sufficiently large to catch or hold dirt). In other embodiments, the unitary design of the copper sheet surface makes the control panel surface easy to clean. In still other embodiments, there is no opening that allows liquid to seep through the copper sheet overlay into the interior of the control panel. The unitary design of the copper sheet overlay can, in some instances, protect the electronic components within the control panel from contamination by dirt or liquids during use and routine cleaning.

EXAMPLES

The following examples are given solely for the purpose of illustration and are not to be construed as a limitation of the present disclosure, as many variations thereof are possible without departing from the spirit and scope of the disclosure.

Example 1

In this Example, copper sheets of various thicknesses and tempers were tested to evaluate the copper sheets' ability to hold an emboss suitable for forming deflection spots. For this test, two alloys of copper were evaluated. Alloy A comprised about 87% copper, 10% nickel, 1% iron, 1% manganese, and 1% zinc by weight of the alloy. Alloy B comprised about 76% copper, 21% nickel, 1% iron, 1% manganese, and 1% zinc by weight of the alloy. For this test, all samples were embossed with a traditional raised emboss pattern, as illustrated in FIG. 3. Nine samples of copper sheets were tested, as shown in Table 2.

TABLE 2

| Sample No. | Alloy | Thickness (inch) | Temper | Surface Appearance | Result |
| --- | --- | --- | --- | --- | --- |
| 1 | A | 0.0015 | Extra Spring | Smooth | Emboss did not always spring back—too soft |
| 2 | A | 0.002 | Spring | Smooth | Emboss worked. Stress marks around emboss |
| 3 | A | 0.002 | Spring | Textured | Emboss worked. Stress marks around emboss |

TABLE 2-continued

| Sample No. | Alloy | Thickness (inch) | Temper | Surface Appearance | Result |
| --- | --- | --- | --- | --- | --- |
| 4 | A | 0.003 | Hard | Smooth | Emboss worked. Stress marks around emboss |
| 5 | A | 0.004 | ½ Hard | Smooth | Emboss did not always spring back—too soft |
| 6 | B | 0.0048 | ¼ Hard | Smooth | Emboss too hard to press. |
| 7 | A | 0.005 | Annealed | Smooth | Emboss dents when pressed—too soft |
| 8 | A | 0.005 | Extra Hard | Smooth | Emboss too hard to press. |
| 9 | A | 0.005 | Extra Hard | Textured | Emboss too hard to press. |

In Example 1, for copper alloy A, it appears that copper sheets with a gauge of 0.0015" and extra spring temper were too soft or too thin for embossed deflection spots, since the embossed areas did not always spring back when depressed. Thicker copper sheets (gauge of 0.004"-0.005") but softer temper (annealed, half-hard) were also too soft, and with the embossed areas not always springing back or even denting when pressed. For copper sheets with a gauge of 0.002"-0.003" made of harder temper copper (hard or spring), the embossed areas had acceptable spring-back when pressed, but the copper sheets showed stress marks and small fractures at the bended edges of the embossed areas after the sheets were embossed. Conversely, thicker copper sheets (gauge=0.005") with extra hard temper formed embossed areas that were hard to depress. Interestingly, copper alloy B, containing a higher amount of nickel than alloy A, had embossed areas that were hard to press at a similar gauge (0.004") and softer temper (¼ hard). From these results, it is clear that the copper alloy, the copper sheet gauge, and the temper of the copper sheet can influence the successful implementation of this inventive copper sheet overlay.

Example 2

In this Example, copper sheets of various thicknesses and tempers were tested to evaluate the copper sheets' ability to hold an emboss suitable for forming deflection spots. For this test, all samples were embossed with a pillow emboss pattern, as illustrated in FIG. 5. Ten samples of copper sheets were tested, as shown in Table 3.

TABLE 3

| Sample No. | Alloy | Thickness (inch) | Temper | Surface Appearance | Result |
| --- | --- | --- | --- | --- | --- |
| 1 | A | 0.0015 | Extra Spring | Smooth | Emboss did not always spring back—too soft |
| 2 | A | 0.002 | Extra Spring | Smooth | Emboss did not always spring back—too soft |
| 3 | A | 0.002 | Spring | Smooth | Emboss worked. A little soft. |
| 4 | A | 0.004 | Hard | Smooth | Emboss worked. |
| 5 | A | 0.004 | ½ Hard | Smooth | Emboss worked |
| 6 | A | 0.004 | Hard | Smooth | Emboss worked |
| 7 | A | 0.006 | Hard | Smooth | Emboss too hard to press. |

TABLE 3-continued

| Sample No. | Alloy | Thickness (inch) | Temper | Surface Appearance | Result |
| --- | --- | --- | --- | --- | --- |
| 8 | A | 0.006 | ½ Hard | Smooth | Emboss worked |
| 9 | A | 0.008 | Hard | Smooth | Emboss too hard to press. |
| 10 | A | 0.008 | ½ Hard | Smooth | Emboss too hard to press. |

In Example 2, copper sheets with a gauge of 0.002" or less and a temper of extra spring were too soft, and the embossed areas did not always spring back. Copper sheets with a gauge of 0.002" and a temper of spring were acceptable, but a little soft, which was of concern for the long-term durability of the deflection spots. Copper sheets with a gauge of 0.004" and a temper of ½ hard or hard could be embossed easily and formed embossed areas that were easy to press and sprang back when depressed. Similarly, copper sheets with a gauge of 0.006" and ½ hard temper worked well. However, copper sheets with a gauge of 0.006" and hard temper had embossed areas that were hard to press. Similarly, copper sheets with a gauge of 0.008" and ½ hard or hard temper also had embossed areas that were hard to press.

The results of Experiments 1 and 2 indicate that both the gauge and temper of copper sheets made from a given copper alloy can influence the suitability of copper sheets used to form the copper sheet overlay of the present invention. It appears, in this example, that copper sheets with a gauge less than about 0.002" are generally too thin, and copper sheets with a gauge of greater than about 0.008" are generally too thick, for the present invention. It also appears, in this example, that copper sheets that are tempered from ¼ hard to spring are generally suitable for the present invention, with the harder tempered coppers better for thinner gauge copper sheets and softer tempered coppers better for thicker gauge copper sheets.

Example 3

In this Example, copper sheets were printed with various ink systems, to test the adhesion of each ink to the copper surface. The inks were screen printed onto the surface of copper sheets made from copper alloy A. After curing, the inks were tested according to ASTM D-3359, "Standard Test Method for Measuring Adhesion by Tape Test," Test Method B. In this test, the printed ink film on the copper surface is cut with a standard cross-hatch tool, and a clean strip of tape is applied firmly to the cut area. The tape is rapidly removed, and the cut area of printed ink on the copper surface is visually evaluated and compared to a standard classification chart to determine the amount of ink that remains adhered to the copper surface. Five types of ink, with and without catalyst, were tested, and the results are shown in Table 4.

TABLE 4

| Sample No. | Ink | Catalyst | Description | Result |
| --- | --- | --- | --- | --- |
| 1 | Nazdar 9600 | No | Solvent based air dry ink system | Poor adhesion |
| 2 | Nazdar 9600 | Yes | Solvent based air dry ink system | Excellent adhesion |
| 3 | Nazdar 1600 | No | UV cured ink system | Poor adhesion |
| 4 | Nazdar 1600 | Yes | UV cured ink system | Good adhesion |
| 5 | Nazdar 3400 | No | UV cured ink system | Poor adhesion |
| 6 | Nazdar 3400 | Yes | UV cured ink system | Good adhesion |

TABLE 4-continued

| Sample No. | Ink | Catalyst | Description | Result |
|---|---|---|---|---|
| 7 | Nazdar 4000 | No | UV cured ink system | Poor adhesion |
| 8 | Nazdar 4000 | Yes | UV cured ink system | Excellent adhesion |
| 9 | Nazdar 1800 | No | UV cured ink system | Poor adhesion |
| 10 | Nazdar 1800 | Yes | UV cured ink system | Good adhesion |

Example 4

In this Example, prototype copper sheet overlays were tested for durability. The prototype copper sheet overlays were made from copper sheeting that corresponds to Sample 4 in Example 2. The copper sheet overlays were embossed with a plurality of round, pillow-embossed deflection spots and printed with graphics using the Nazdar 4000 ink system with catalyst. The copper sheet overlays were then assembled into control panel units suitable for use in a hospital setting. The copper sheet overlays of the control panels were tested for tested for: a) exposure to cleaning solutions, b) wipe testing with cleaning solutions, and c) switch operation (deflection) durability.

Exposure to Cleaning Solutions and Wipe Testing

To test the durability of the copper sheet overlays of the control panels, sponges saturated with a diluted 1:10 bleach solution were placed on the copper sheet overlay of the test control panels. Each control panel with sponge was carefully sealed in a plastic bag, and the copper sheet overlay remained in contact with the bleach-soaked sponge for 24 hours. The copper sheet overlay was examined after 24 hours. The copper sheet overlay was wiped with a cotton-blend cloth using medium hand pressure for 500 cycles, where each cycle was a pass across the copper sheet overlay and back.

The experiment was repeated on each control panel for a second 24-hour period. During the second trial period, the sponge saturated with bleach was placed on a cotton cloth, and the sponge and cloth were placed cloth-side down on the copper sheet overlay of the test control panels. Each control panel with sponge and cloth was again sealed in a plastic bag for a second 24 hour trial period. The copper sheet overlay was again examined and wiped as described above.

The graphics and embossing on the copper sheet overlays withstood exposure to the bleach solution and the wiping test. It was observed that the copper sheet overlay developed a somewhat mottled appearance after being exposed to the saturated sponge for 24 hours. However, this was merely a cosmetic problem and did not affect the integrity of the copper sheet overlay, the printed graphics, or the operation of the control panel. It was thought that the mottled appearance might be due to pooling of the bleach solution within the pores and along the edges of the sponge, which would not be a likely problem in actual use. To test this theory, a cloth was placed between the sponge and copper sheet overlay for the second 24-hour trial period, because the cloth was expected to distribute the bleach solution more evenly over the copper sheet overlay. No additional mottling on the copper sheet overlays was observed after the second 24-hour trial period.

Switch Operation Durability Testing

The test control panels were clamped into a switch life cycle tester, and a finger-test probe was located over a deflection spot on the copper sheet overlay. The switch life cycle tester was set to press the probe onto the deflection spot at a load of 32 ounces (900 g). The switch life cycle tester was set to travel about 0.1 inch as it pressed the deflection spot. The switch life cycle tester was set to execute 300,000 cycles, which represents 100 switch activations per day for 300 days per year for 10 years. The switch life cycle tester was paused at intervals during the 300,000 cycles to allow the copper sheet overlay to be examined for signs of wear or damage.

After 300,000 cycles, there was no visible change in the appearance or function of the copper sheet overlay of the control panel (i.e., no thinning, cracking, bending, or crumpling). The deflection spots on the test control panels remained fully functioning and intact during and after the cycle testing.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative compositions and methods, and illustrative examples shown and described. Accordingly, departures may be made from such details without departing from the spirit or scope of the applicant's general disclosure herein.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

To the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, and 10) contained within the range.

What is claimed is:

1. A control panel surface comprising an antimicrobial copper sheet overlay comprising metallic copper or a metallic copper alloy of unitary design, said copper sheet overlay having at least one deflection spot with a vertical travel length of from 0.1 mm to 5 mm,
    wherein there are no gaps or crevices in the copper sheet overlay around the at least one deflection spot, and
    wherein the antimicrobial copper sheet overlay is printed with at least one ink to form at least one graphic on an area other than the at least one deflection spot.

2. The control panel surface of claim 1, wherein the antimicrobial copper sheet overlay has a thickness t from 0.002 inches to 0.008 inches.

3. The control panel surface of claim 1, wherein the antimicrobial copper sheet overlay comprises copper or a copper alloy comprising from 60 wt % to 100 wt % copper.

4. The control panel surface of claim 3, wherein the copper or copper alloy is tempered to a temper selected from the group consisting of ¼ hard, ½ hard, ¾ hard, hard, extra hard, and spring.

5. The control panel surface of claim 3, wherein the copper or copper alloy has a tensile strength from 350 $N/mm^2$ to 600 $N/mm^2$.

6. The control panel surface of claim 1, wherein the antimicrobial copper sheet overlay comprises more than one deflection spot.

7. The control panel surface of claim 1, wherein one or more of the at least one deflection spot is embossed.

8. The control panel surface of claim 1, wherein the antimicrobial copper sheet overlay is part of a control panel.

9. A control panel comprising:
   a. a control panel surface comprising an antimicrobial copper sheet overlay comprising metallic copper or a metallic copper alloy of unitary design, said copper sheet overlay having at least one deflection spot with a vertical travel length of from 0.1 mm to 5 mm, and
   b. a circuit board comprising at least one switch,
wherein there are no gaps or crevices in the copper sheet overlay around the at least one deflection spot,
wherein the at least one deflection spot is located over the at least one switch on the circuit board, and
wherein the antimicrobial copper sheet overlay is printed with at least one ink to form at least one graphic on an area other than the at least one deflection spot.

10. The control panel of claim 9, wherein the control panel surface comprises more than one antimicrobial copper sheet overlays.

11. The control panel of claim 9, wherein the control panel comprises more than one circuit board.

12. The control panel of claim 9, wherein the antimicrobial copper sheet overlay has a thickness t from 0.002 inches to 0.008 inches.

13. The control panel of claim 9, wherein the antimicrobial copper sheet overlay comprises copper or a copper alloy comprising from 60 wt % to 100 wt % copper.

14. The control panel of claim 13, wherein the copper or copper alloy is tempered to a temper selected from the group consisting of ¼ hard, ½ hard, ¾ hard, hard, extra hard, and spring.

15. The control panel of claim 13, wherein the copper or copper alloy has a tensile strength from 350 $N/mm^2$ to 600 $N/mm^2$.

16. The control panel of claim 9, wherein the antimicrobial copper sheet overlay comprises more than one deflection spots.

17. The control panel of claim 9, wherein one or more of the at least one deflection spot is embossed.

18. The control panel of claim 9, wherein the at least one deflection spot can withstand a finger press at a force of 4.5 N for at least 100,000 cycles without the antimicrobial copper sheet overlay being damaged.

19. A method of operating an electronic device, comprising:
   a. providing an electronic device;
   b. providing a control panel intended to operate the electronic device, wherein the control panel comprises:
      i. a control panel surface, wherein the control panel surface comprises an antimicrobial copper sheet overlay comprising metallic copper or a metallic copper alloy of unitary design, said copper sheet overlay having at least one deflection spot with a vertical travel length of from 0.1 mm to 5 mm, wherein there are no gaps or crevices in the copper sheet overlay around the at least one deflection spot, and wherein the antimicrobial copper sheet overlay is printed with at least one ink to form at least one graphic on an area other than the at least one deflection spot; and
      ii. a circuit board located under the control panel surface, wherein the circuit board comprising at least one switch located under the at least one deflection spot;
   c. pressing the at least one deflection spot on the antimicrobial copper sheet overlay to operate the electronic device.

20. The method of claim 19, wherein one or more of the at least one deflection spot is embossed.

21. The method of claim 19, wherein the antimicrobial copper sheet overlay has a thickness t from 0.002 inches to 0.008 inches.

22. The method of claim 19, wherein the antimicrobial copper sheet overlay comprises copper or a copper alloy comprising from 60 to 100 wt % copper.

23. The method of claim 19, wherein the antimicrobial copper sheet overlay comprises more than one deflection spot and the circuit board comprises more than one switch.

* * * * *